US008686857B2

(12) United States Patent
Harada

(10) Patent No.: US 8,686,857 B2
(45) Date of Patent: Apr. 1, 2014

(54) WIRELESS TAG COLLECTIVE READING DEVICE, AND NETWORK ARTICLE MANAGEMENT SYSTEM

(75) Inventor: Hideaki Harada, Tokyo (JP)

(73) Assignee: Hideaki Harada (JP)

( * ) Notice: Subject to any disclaimer, the term of this patent is extended or adjusted under 35 U.S.C. 154(b) by 282 days.

(21) Appl. No.: 13/271,602

(22) Filed: Oct. 12, 2011

(65) Prior Publication Data

US 2012/0025988 A1  Feb. 2, 2012

Related U.S. Application Data

(63) Continuation of application No. PCT/JP2010/056717, filed on Apr. 14, 2010.

(30) Foreign Application Priority Data

Apr. 14, 2009  (JP) .................................. 2009-098433

(51) Int. Cl.
*G08B 13/14*  (2006.01)
(52) U.S. Cl.
USPC ................... 340/572.1; 340/10.1; 340/572.7; 340/568.1
(58) Field of Classification Search
USPC ..................................................... 340/572.1
See application file for complete search history.

(56) References Cited

U.S. PATENT DOCUMENTS

| | | | |
|---|---|---|---|
| 7,187,288 B2 * | 3/2007 | Mendolia et al. .......... | 340/572.1 |
| 2003/0216969 A1 * | 11/2003 | Bauer et al. ..................... | 705/22 |
| 2008/0122615 A1 * | 5/2008 | Shoenfeld ..................... | 340/540 |

FOREIGN PATENT DOCUMENTS

| | | |
|---|---|---|
| CN | 1627322 A | 6/2005 |
| JP | 2001-356688 | 12/2001 |
| JP | 2006-079202 | 3/2006 |
| JP | 2006-252099 | 9/2006 |
| JP | 2007-034560 | 2/2007 |
| JP | 2007-059958 | 3/2007 |
| JP | 2007-156953 | 6/2007 |
| JP | 2007-333466 | 12/2007 |
| JP | 2008-071071 | 3/2008 |
| JP | 2008-197842 | 8/2008 |

OTHER PUBLICATIONS

News Release, "Development of Sample Tube (Test Tube) Management System Using "Data-Writable Test Tube" Small RFID Chip", http://www.maxei.co.jp/news/pdf/060714Jpn.pdf, Jul. 2006.

(Continued)

*Primary Examiner* — Kerri McNally
(74) *Attorney, Agent, or Firm* — Harness, Dickey & Pierce, P.L.C.

(57) ABSTRACT

A wireless tag collective reading device of this invention comprises a rack to store the wireless-tag-equipped articles which are mounted on the wireless-tag-equipped article by printing a chip portion and an antenna portion connected to the chip portion, the chip portion emitting tag information in response to electromagnetic waves, and an antenna unit which applies, to the wireless-tag-equipped articles stored in the rack, electromagnetic waves for the emission of the tag information, and receives electromagnetic waves for the tag information emitted from the wireless tag, wherein the device controls the directivity, intensity, and phase of the electromagnetic waves emitted from the antenna unit to apply the electromagnetic waves to the wireless-tag-equipped article at a given position stored in the rack, controls the relative positions of the antenna unit and the rack, and reads the tag information from a signal received by the antenna unit.

7 Claims, 46 Drawing Sheets

(56) References Cited

OTHER PUBLICATIONS

Translation of the International Search Report for PCT/JP2010/056717 (in English), mailed Nov. 15, 2011; ISA/JP.

Translation of the International Preliminary Report on Patentability for PCT/JP2010/056717 (in English), mailed Nov. 15, 2011; ISA/JP.

Chinese Office Action for Application No. 2010 80017004.0 dated Sep. 23, 2013 with English translation (4 pages).

* cited by examiner

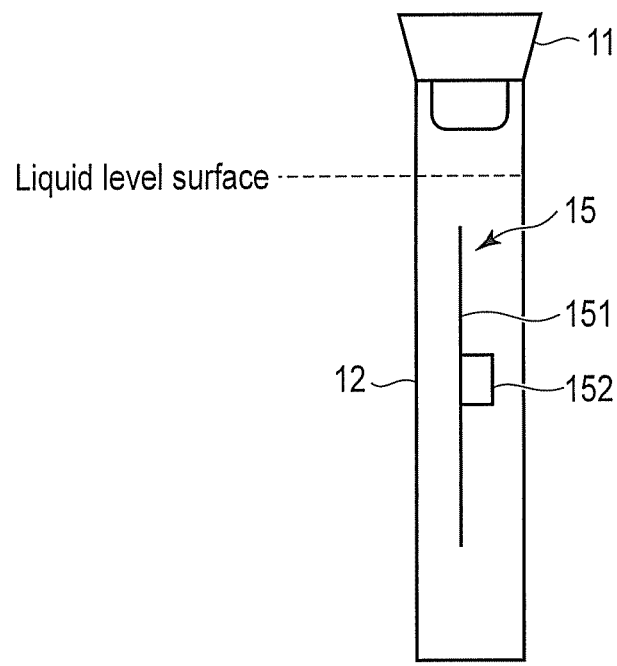
F I G. 2
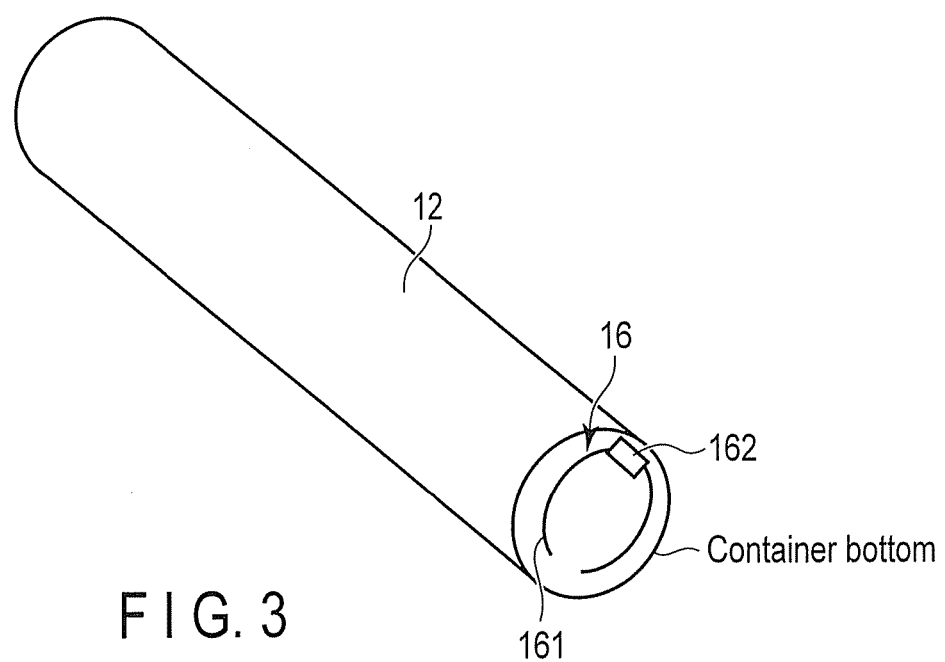
F I G. 3

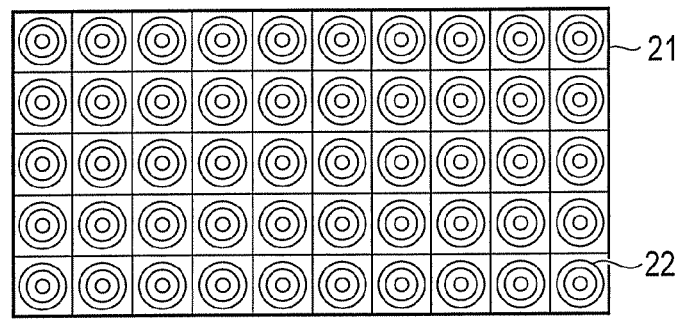
F I G. 4A
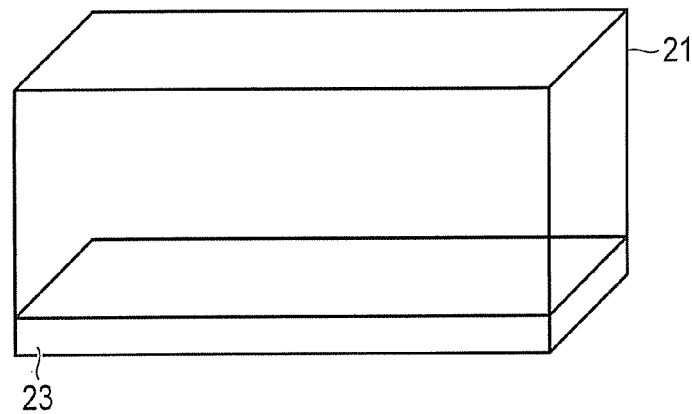
F I G. 4B
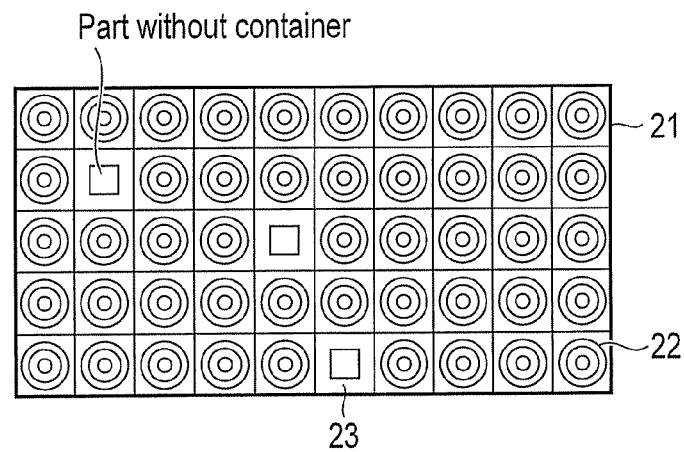
F I G. 4C

Part without container

Switch detecting result: OFF OFF OFF OFF OFF OFF OFF OFF OFF OFF

Switch detecting result: ON ON OFF ON OFF OFF ON ON ON ON

Place where container 22 is not in rack 21

Probe 2311 is generally separated from switch 2312 by, e.g., spring, and switch is therefore off Off-state On-state Off-state On-state

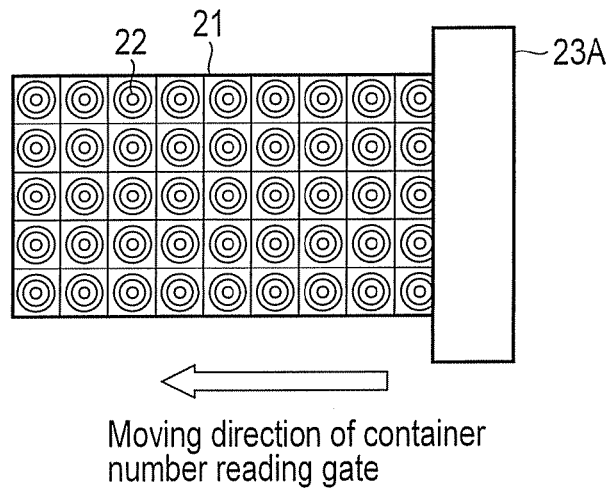
Moving direction of container number reading gate
F I G. 12A
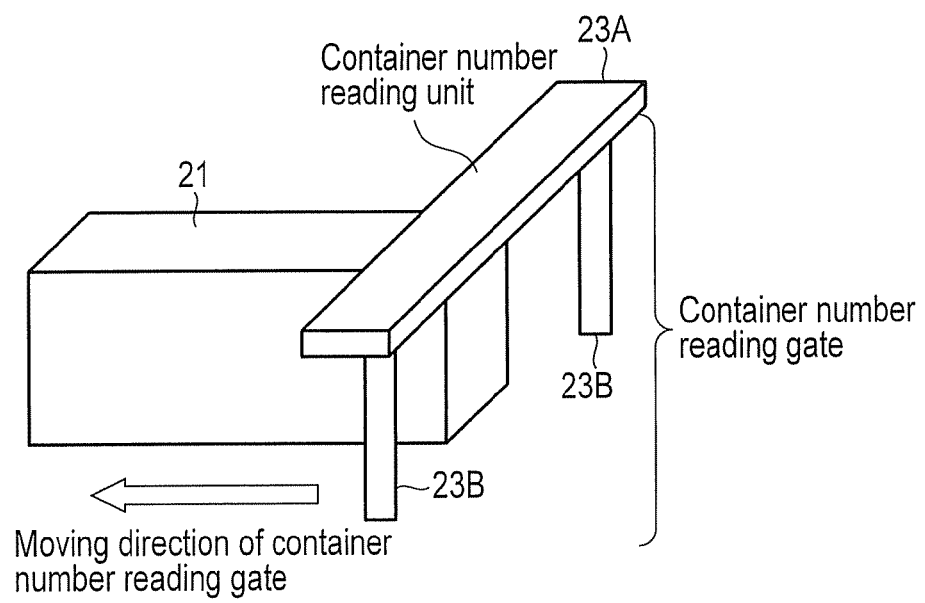
F I G. 12B

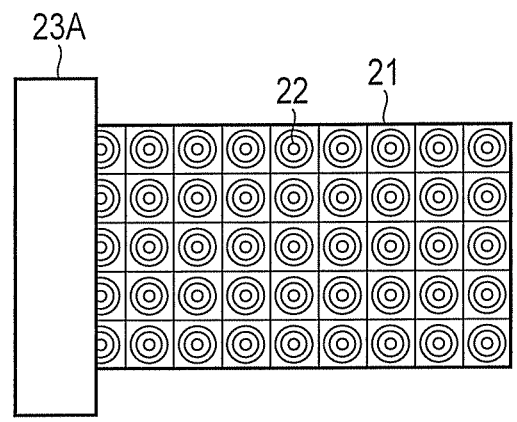
F I G. 13A
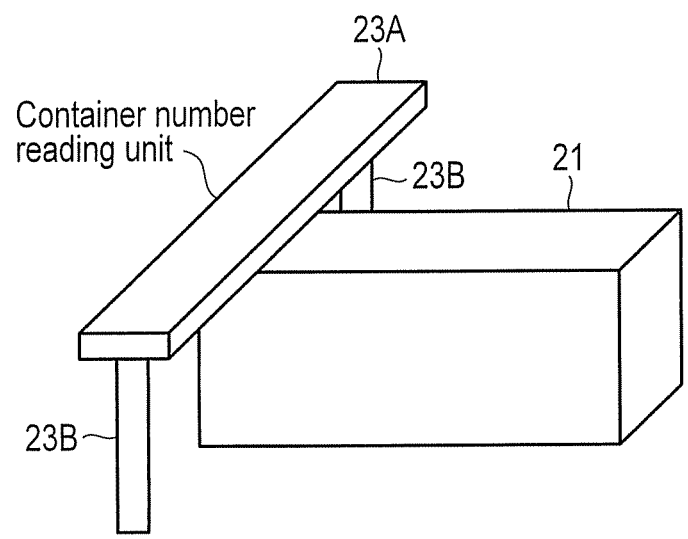
F I G. 13B

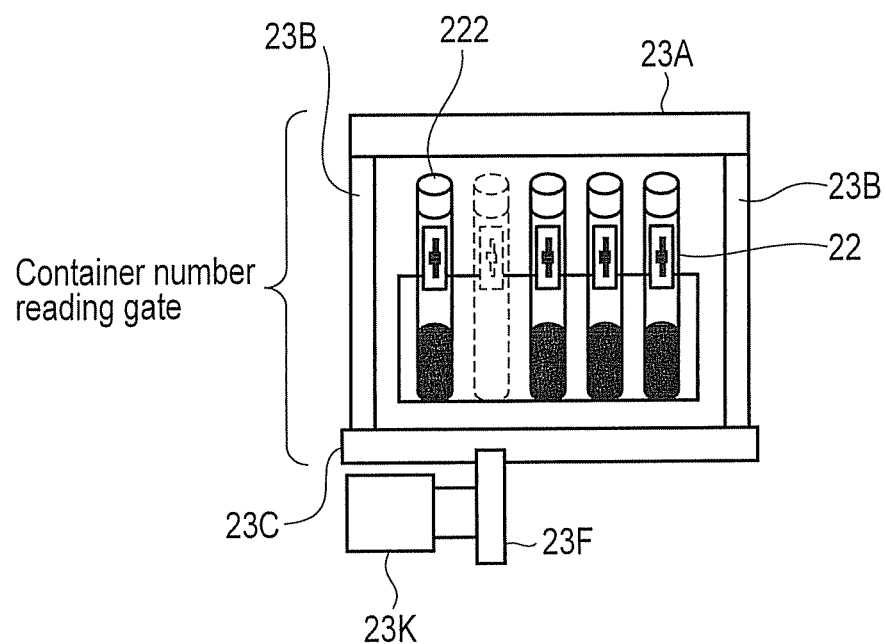
F I G. 14C

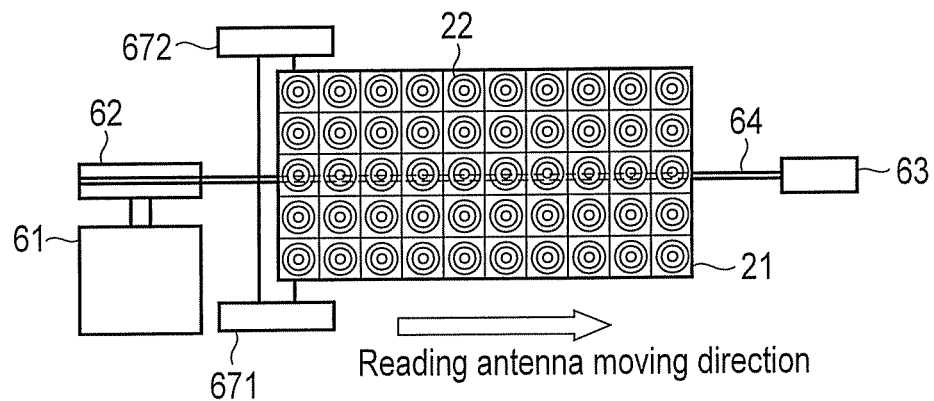
F I G. 16A
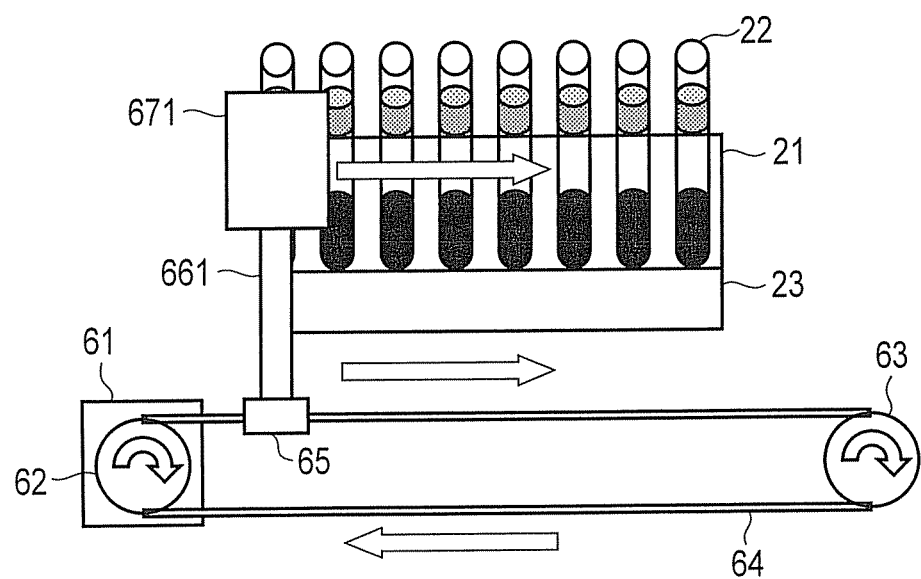
F I G. 16B

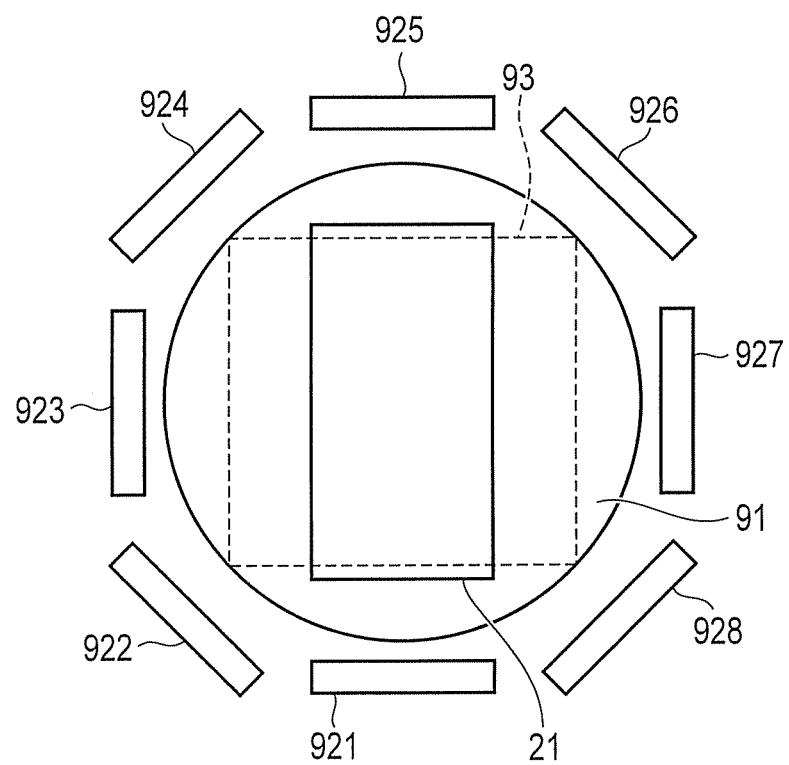
F I G. 19

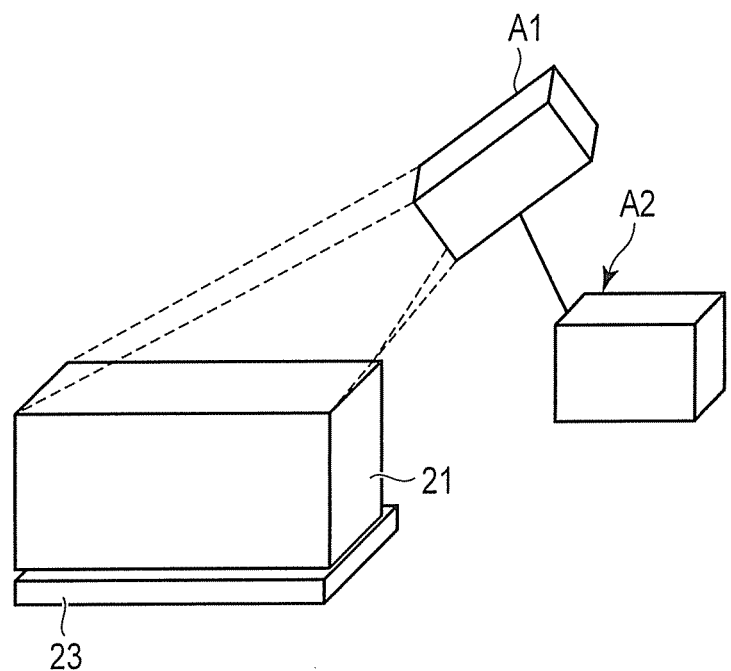
F I G. 20A
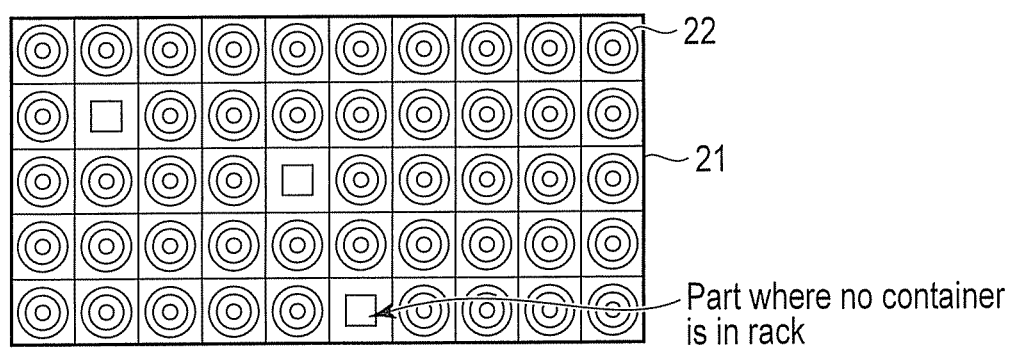
Part where no container is in rack
F I G. 20B

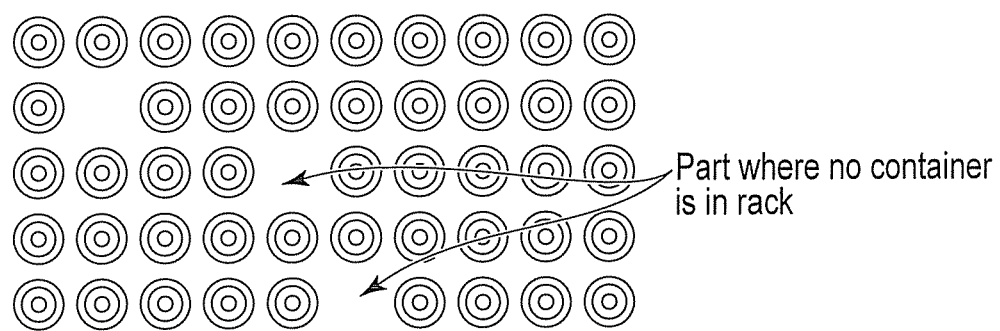
F I G. 20C

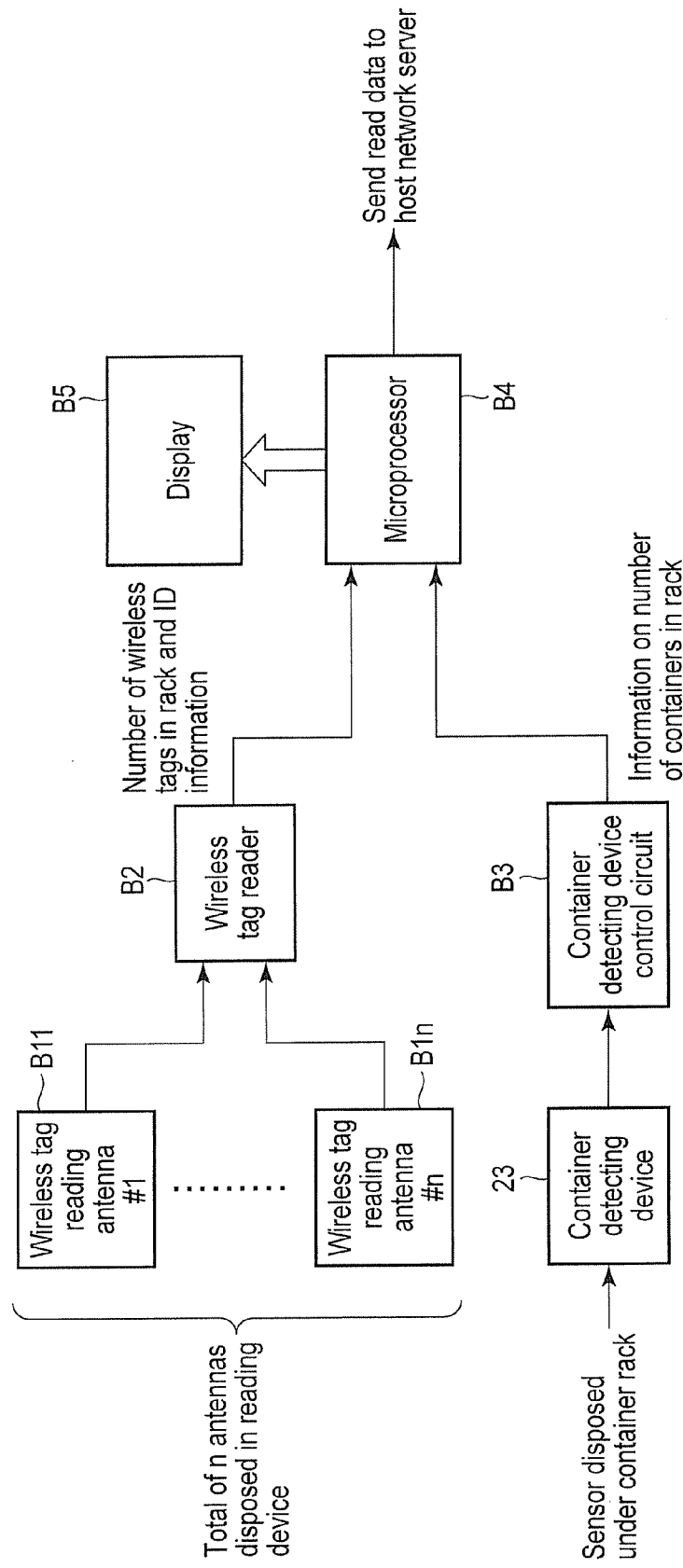
F I G. 21

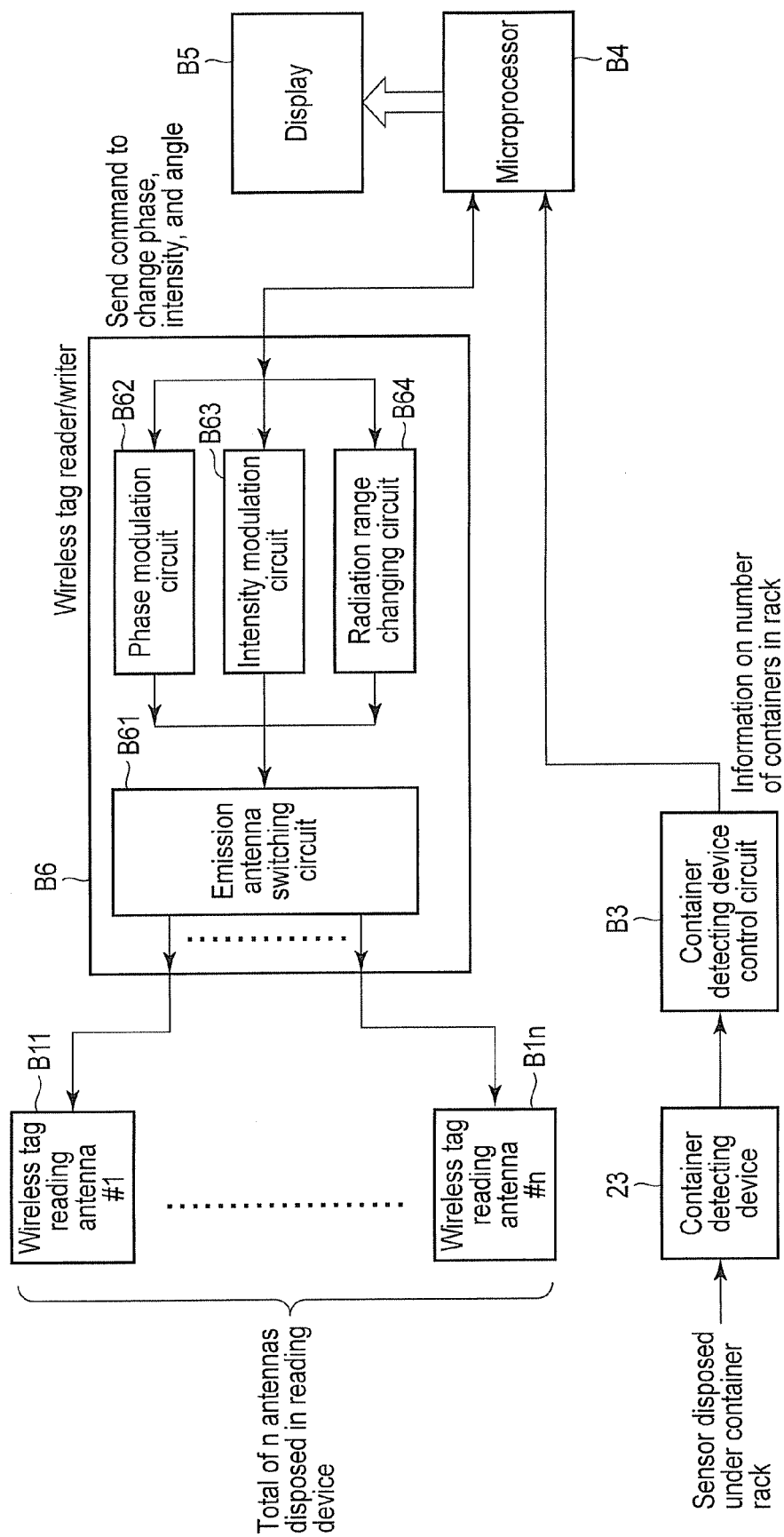
F I G. 24

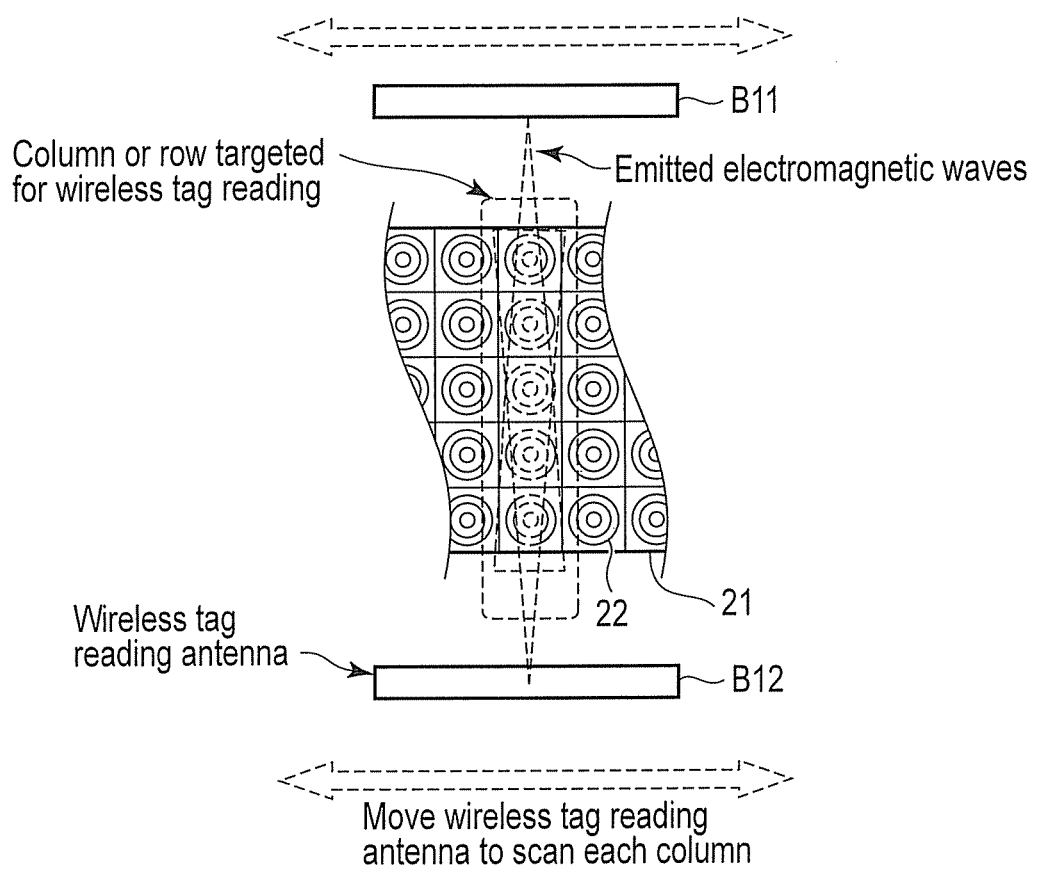
F I G. 25A

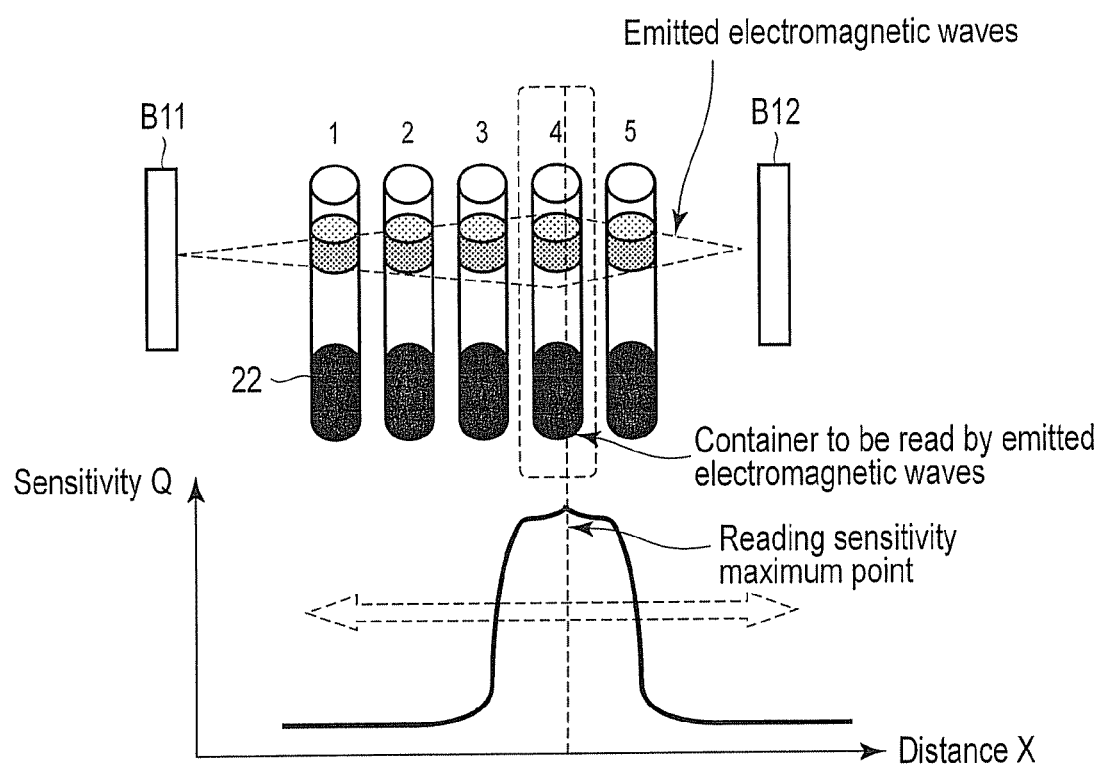
F I G. 25B

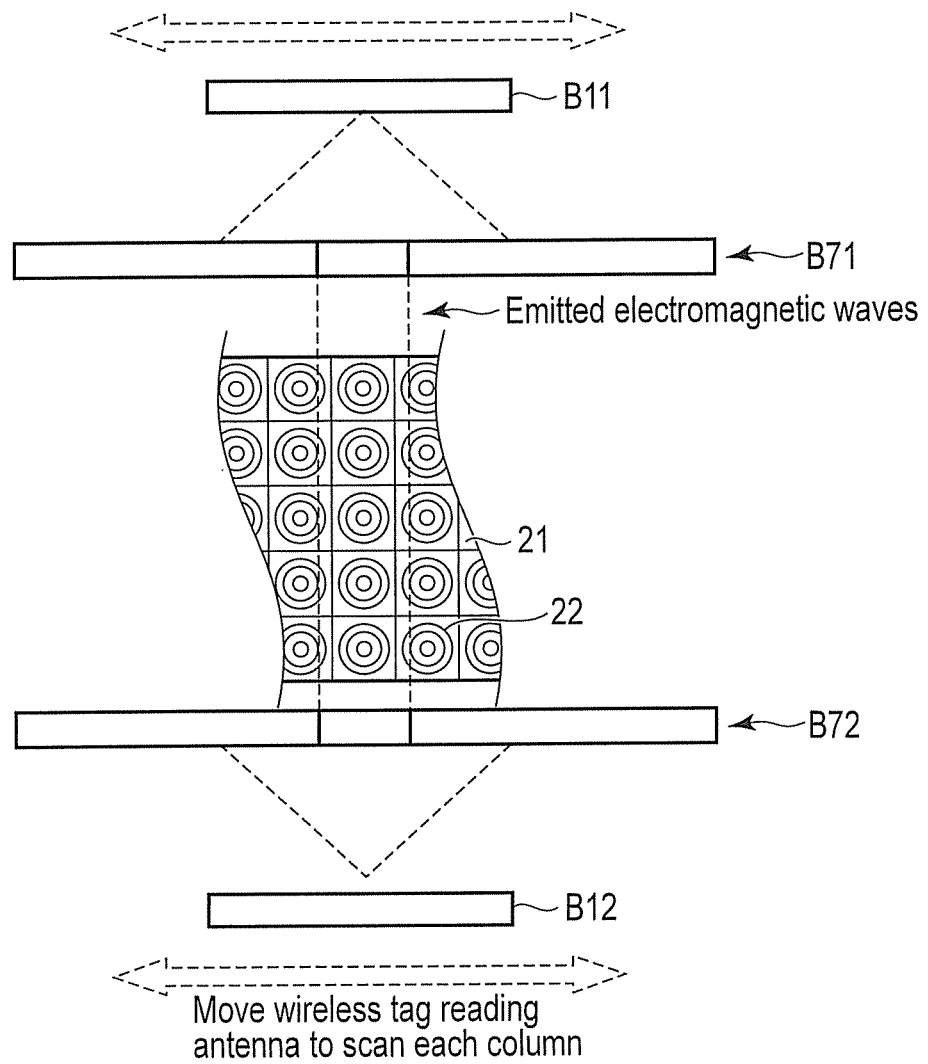
F I G. 26

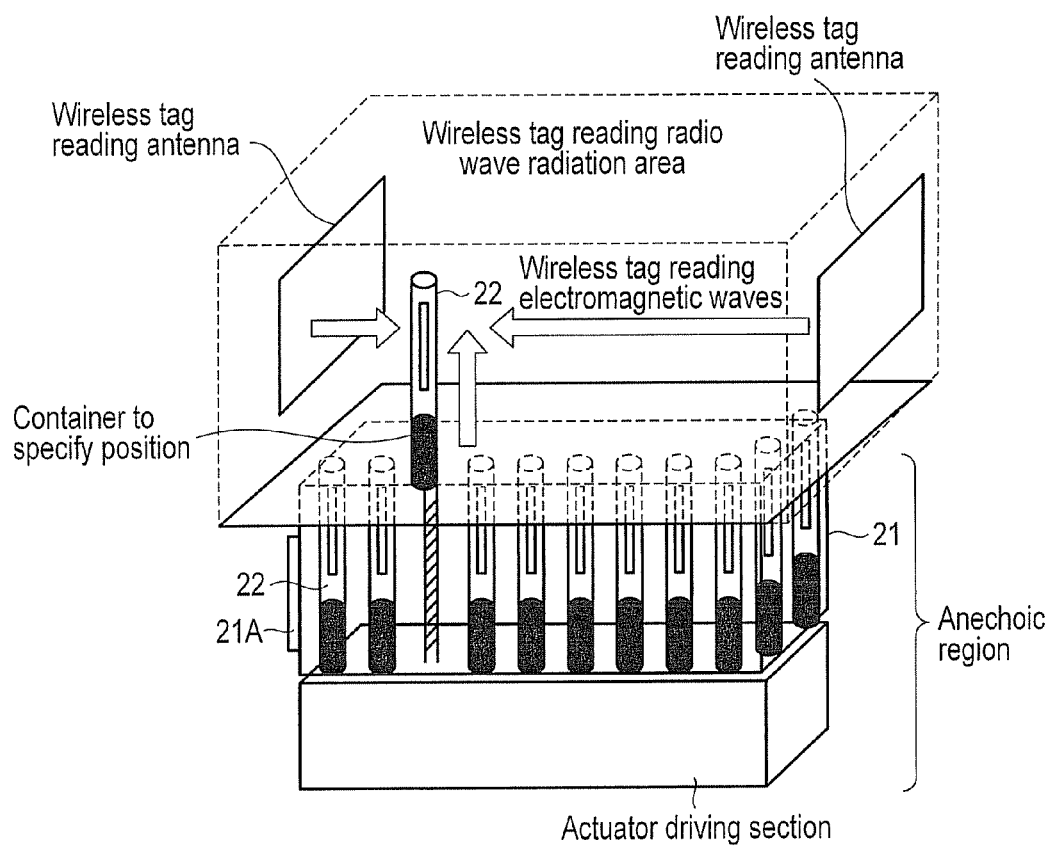
F I G. 31B

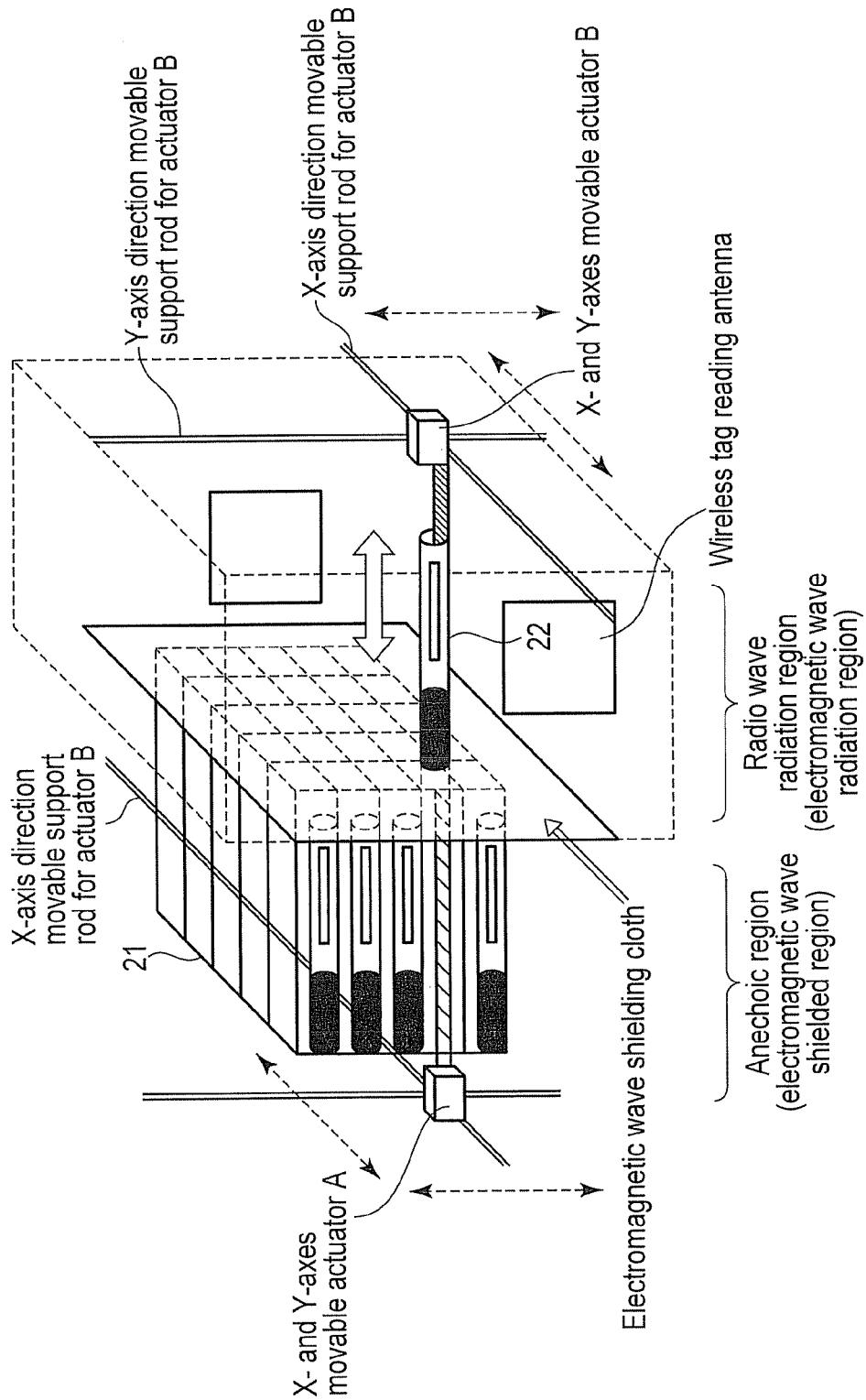
F I G. 32

■ Rack ID: Internal position of number 1234-5678-9012 is indicated

Column number / Row number

|  | A | B | C | D | E | F | G | H | I | J |
|---|---|---|---|---|---|---|---|---|---|---|
| 1 | 1 | 6 | 11 | 16 | 21 | 26 | 31 | 36 | 41 | 46 |
| 2 | 2 | 7 | 12 | 17 | 22 | 27 | 32 | 37 | 42 | 47 |
| 3 | 3 | 8 | 13 | 18 | 23 | 28 | 33 | 38 | 43 | 48 |
| 4 | 4 | 9 | 14 | 19 | 24 | 29 | 34 | 39 | 44 | 49 |
| 5 | 5 | 10 | 15 | 20 | 25 | 30 | 35 | 40 | 45 | 50 |

(E.g.) click on number 33

Click on blood collection tube for details

This test tube rack is stored in third column from right on second shelf of locker No. 234 in room 101 of first basement of ward A

F I G. 33A

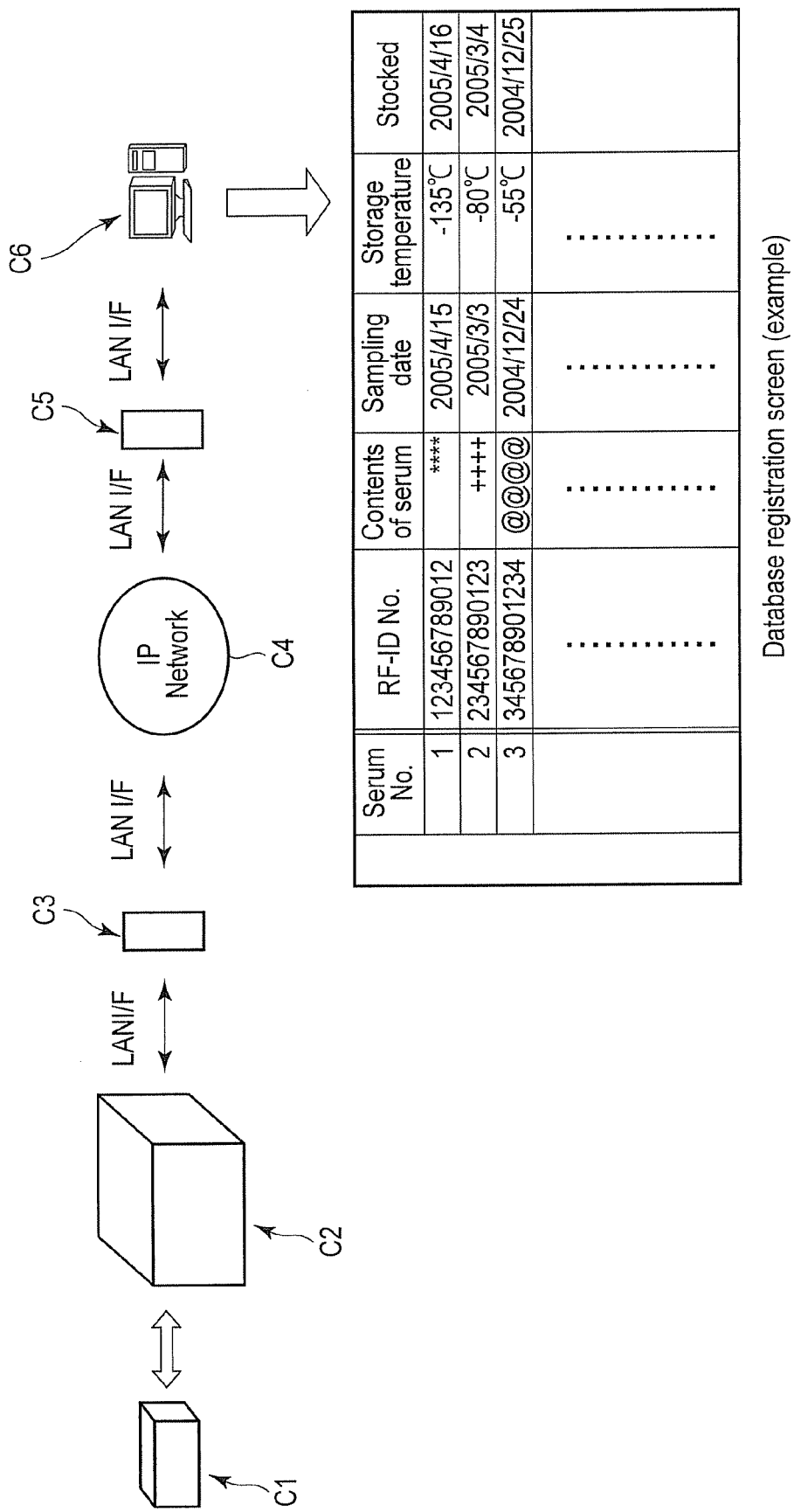
F I G. 34

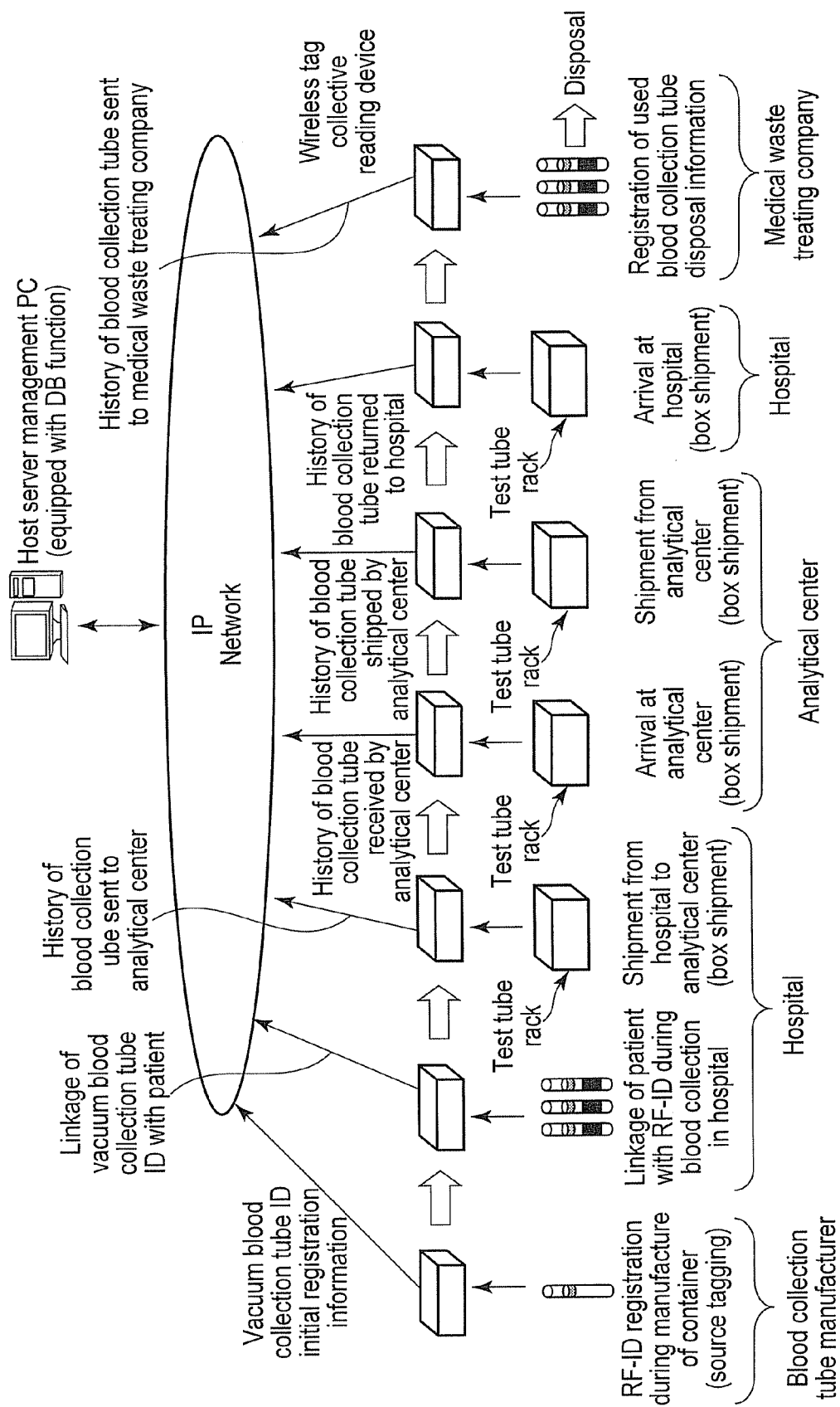
F I G. 35

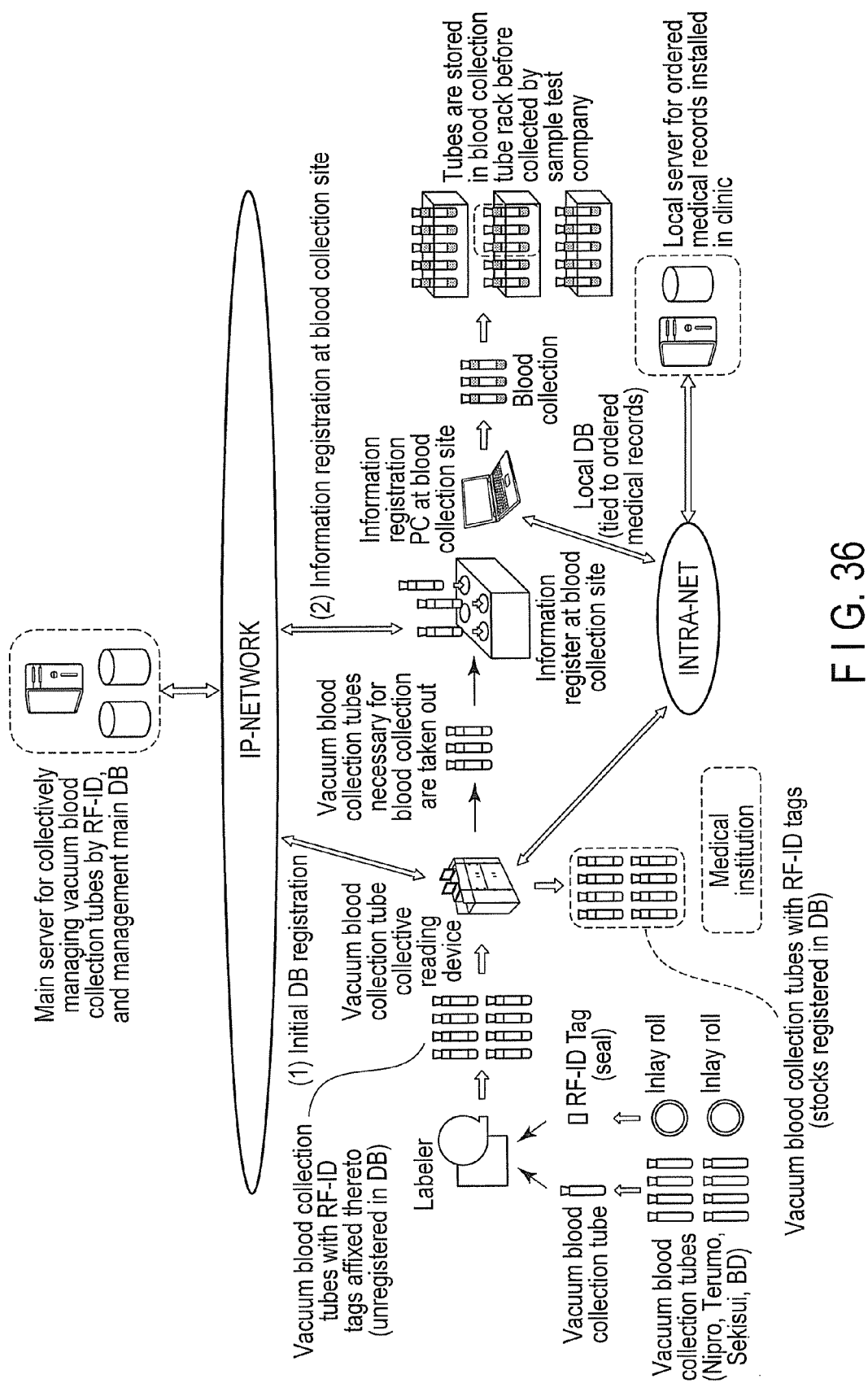
F I G. 36

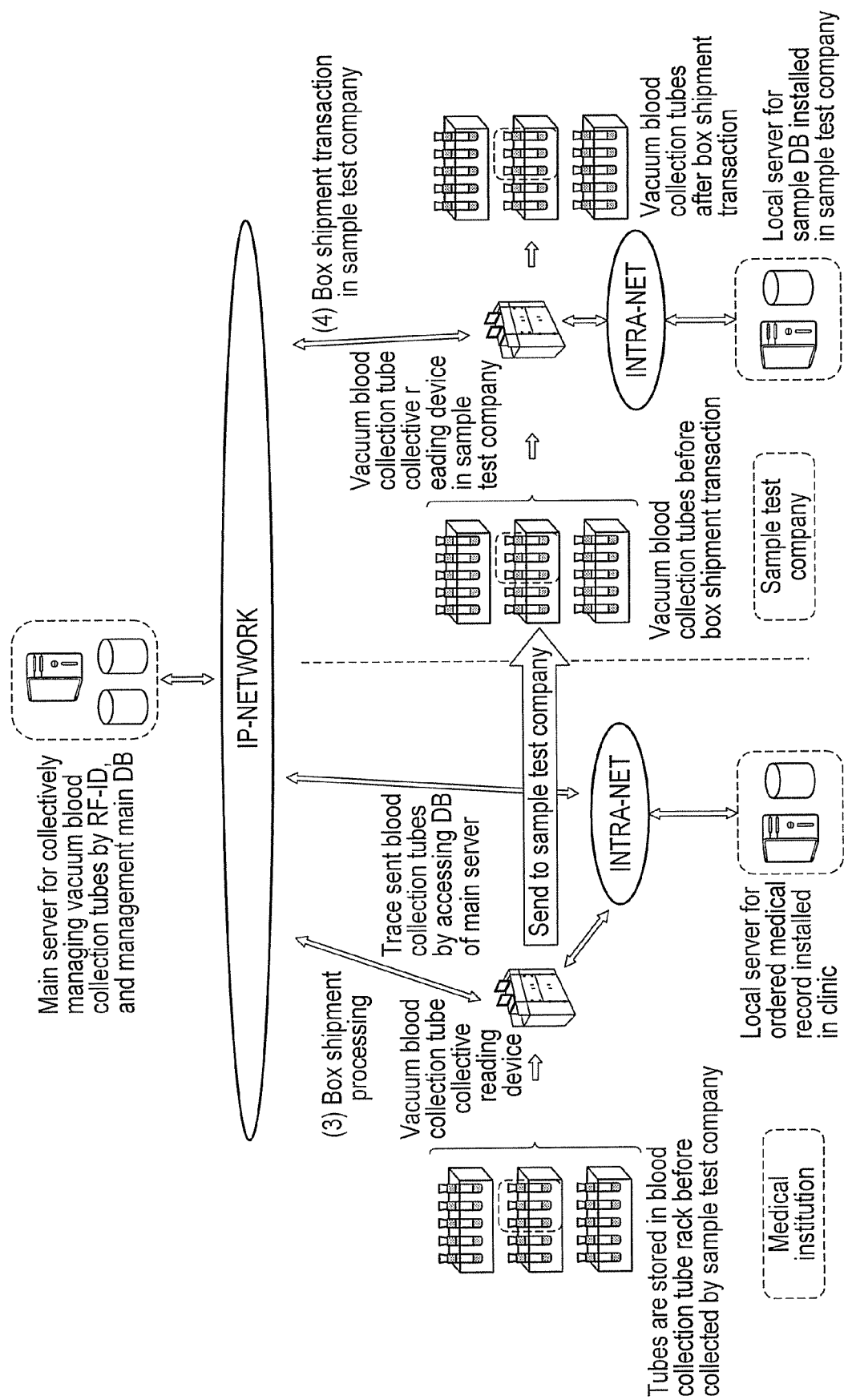
F I G. 37

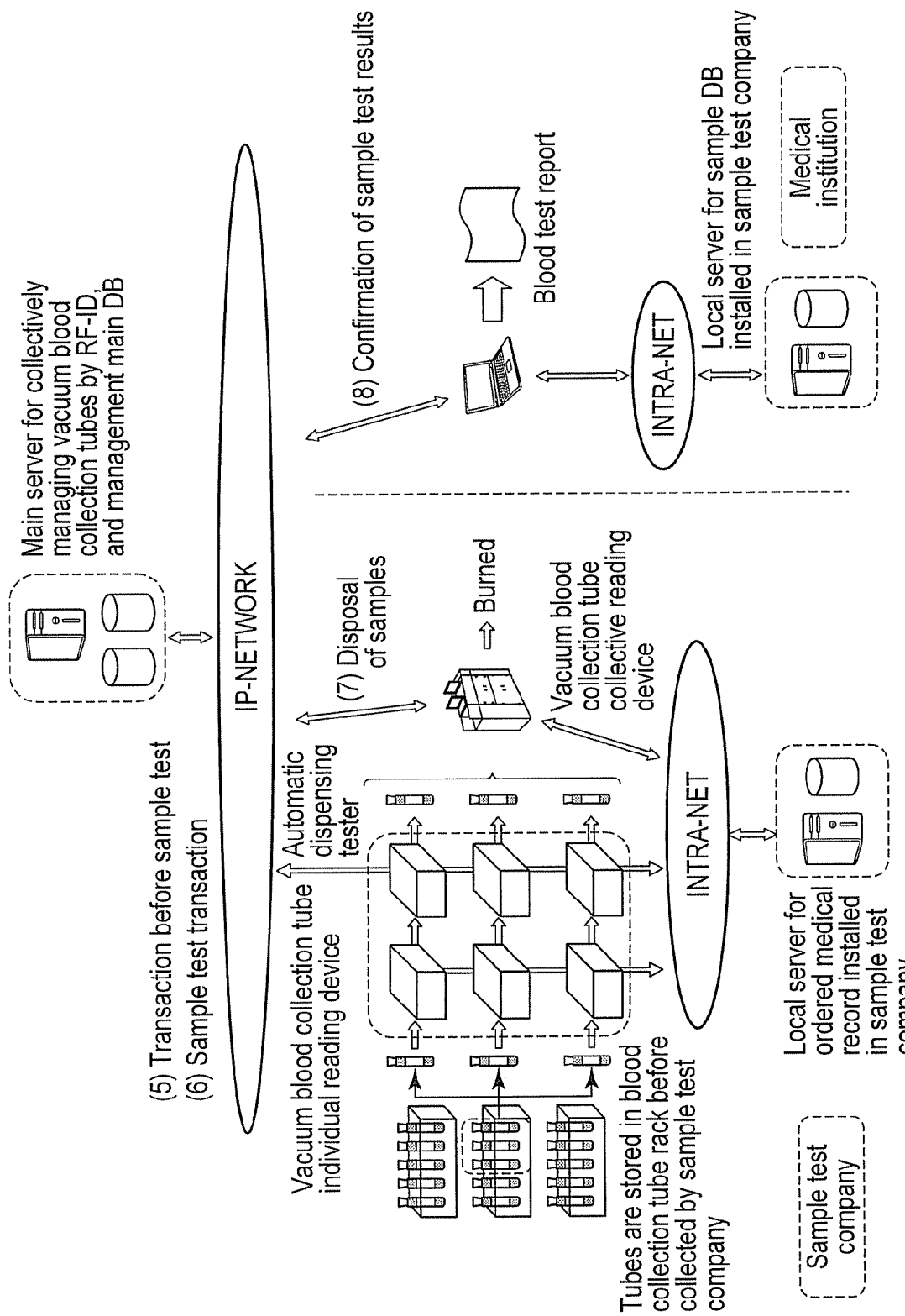
F I G. 38

Top view of RF-ID tag
with bar code

Sectional structure of RF-ID tag
with bar code

Bar code label
F I G. 39C
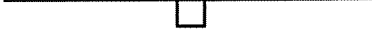
RF-ID tag inlay
F I G. 39D
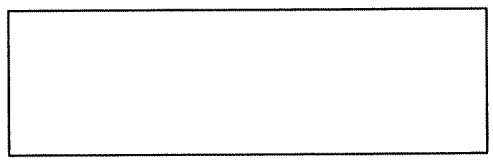
Cold-proof and heat-resistant
adhesive tape or paste
F I G. 39E

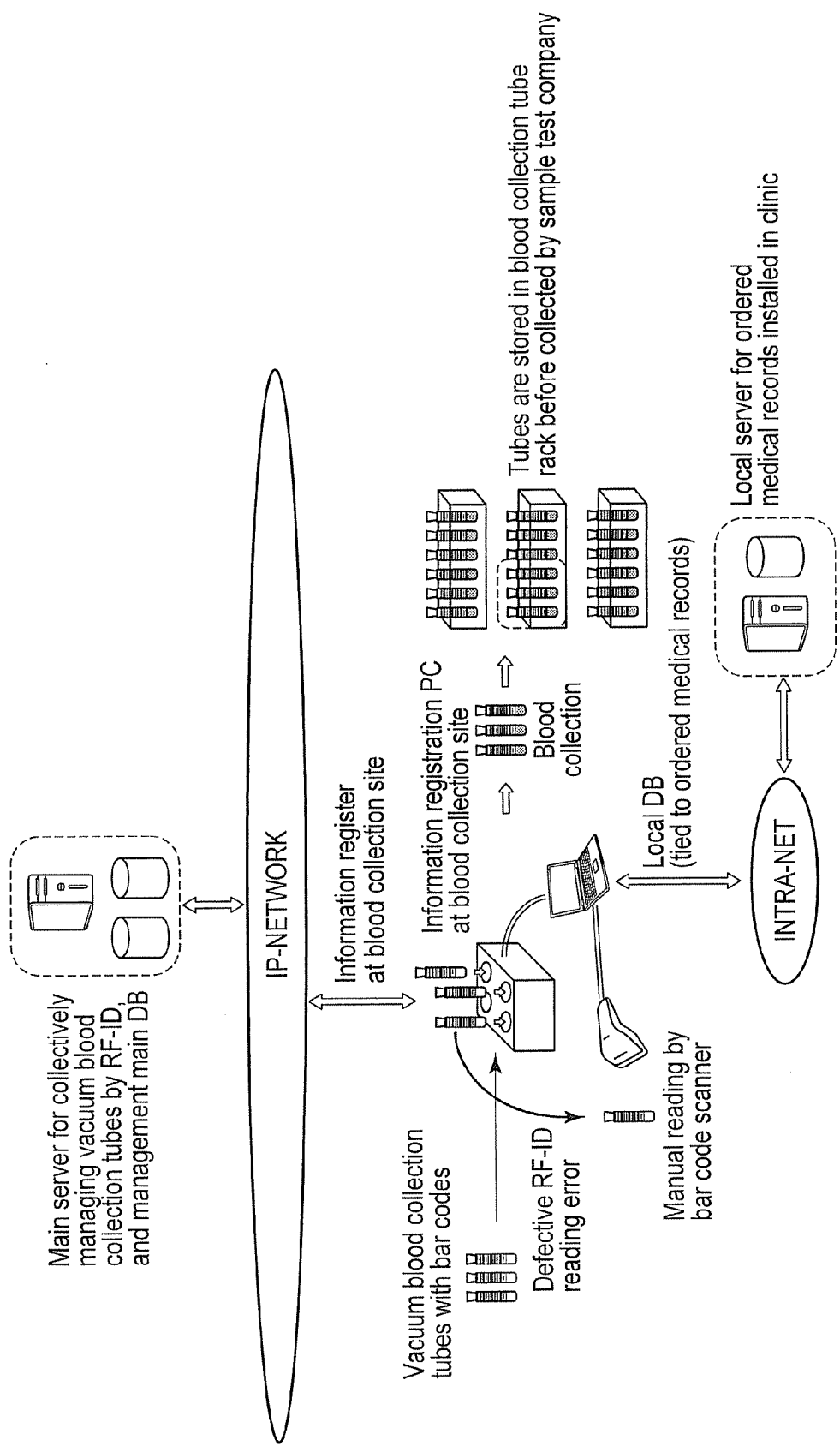
F I G. 40

WIRELESS TAG COLLECTIVE READING DEVICE, AND NETWORK ARTICLE MANAGEMENT SYSTEM

CROSS REFERENCE TO RELATED APPLICATIONS

This application is a Continuation Application of PCT Application No. PCT/JP2010/056717, filed Apr. 14, 2010 and based upon and claiming the benefit of priority from prior Japanese Patent Application No. 2009-098433, filed Apr. 14, 2009, the entire contents of all of which are incorporated herein by reference.

BACKGROUND OF THE INVENTION

1. Field of the Invention

The present invention relates to a wireless-tag-equipped article equipped with a wireless tag which emits tag information in response to electromagnetic waves, a wireless tag collective reading device which collectively reads tag information for all wireless-tag-equipped articles from a rack for storing the articles, an in-rack container position detector which automatically detects the location of each container in a rack and registers the result on a database, and a network article management system which uses a management server on a network to manage reading results by a wireless tag collective reading device and detection results by an in-rack container position detector.

2. Description of the Related Art

At present, products adapted to a 13.56 MHz band, a 2.45 GHz band, and a UHF band (950 MHz band) are prepared for various purposes as radio frequency identification (RF-ID) tags known as wire tags. The RF-ID tags of the respective frequencies are used for intended purposes.

In order to attach the wireless tags to containers such as test tubes or vacuum blood collection tubes, there have heretofore been suggestions to affix the wireless tag with seals or to bury the wireless tag in a material that constitutes the container (e.g., see Jpn. Pat. Appln. KOKAI Publication No. 2001-356688).

There has also been a suggestion for a technique to read, by radio waves, all wireless tags of closely arranged articles (e.g., see Jpn. Pat. Appln. KOKAI Publication No. 2007-156953 and Jpn. Pat. Appln. KOKAI Publication No. 2008-071071, and Development of sample tube (test tube) management system using "data-writable test tube" small RFID chip (news release July, 2006) Internet <http://www.maxei.co.jp/news/pdf/060714Jpn.pdf>). This reading technique is called a near-field (near region reading) technique that uses one or both (electromagnetic waves) of radio waves and a magnetic field. The wireless tags have heretofore been studied to solve the issue of how to read from a long distance. This is referred to as a far-field (long-distance region reading) technique. However, for example, at a cash register in a supermarket, there are a great number of articles in a small space, and there may also be containers containing water in the rear. In this case, it has been difficult for the conventional techniques to collectively read these articles.

A technique developed to solve this issue is called the near-field (near region reading) technique. This technique utilizes magnetic field emission in addition to the conventional radio wave emission to read wireless tags, and thereby makes it possible to read wireless tags affixed to a great number of closely arranged containers containing water in the rear.

However, there has not yet been suggested any specific method to ascertain the actual number of closely arranged containers without a reading error. This is a major problem in applications where a high degree of reliability is required, for example, in the medical field. For example, under the present circumstances, when vacuum blood collection tubes with wireless tags affixed thereto are closely stored in a rack, it is not always possible to judge whether the number read by radio electromagnetic waves corresponds to the actual number. Another extremely difficult problem is to judge whether a wireless tag is broken or whether a wireless tag is readable.

Furthermore, there have been no systems produced to automatically know the arrangement of containers such as vacuum blood collection tubes closely stored in a rack and register the arrangement on a database. This is an extremely important function for regular inventories of containers such as vacuum blood collection tubes. This process has heretofore been manually carried out one by one; resulting in considerable man-hour and costs.

BRIEF SUMMARY OF THE INVENTION

Technical Problem

According to conventional methods for wireless tags, a wireless tag is affixed to an article to be used, for example, with a seal, or the wireless tag is buried in a material that constitutes the article. However, the disadvantage of affixing a wireless tag with a seal is that the seal is detached or damaged by an extremely low temperature or humidity. The disadvantages of burying a wireless tag in an article to be used are increased costs resulting from the complicated process of manufacturing the article, and possible unstable accuracy of reading the wireless tag caused by a dielectric constant changing with the material of the article.

According to a method employed by a conventional device for collectively reading articles that use wireless tags, radio waves, a magnetic field, or electromagnetic waves are applied to a wireless tag from an antenna, and information from the wireless tag is read (near-field technique). In this case, for example, when test tubes with wireless tags affixed thereto that are stored in a test tube rack are collectively read, the number of test tubes actually stored in the rack can only be judged by the reading result of electromagnetically read wireless tags. Therefore, when the wireless tag is damaged, or when the wireless tag is functionally normal but the wireless tag cannot respond to the radio waves, magnetic field, or electromagnetic waves from the wireless tag reading antenna due to the environment in which the wireless tag is placed (the direction or position of the antenna of the wireless tag), it is difficult to instantaneously know the number of reading errors, and it also takes much trouble and is difficult to specify which container is unsuccessfully read. Moreover, no specific method has yet been disclosed to ensure 100% traceability of articles with regard to the process for a wireless tag judged to be broken.

This invention has been made in view of such circumstances, and has four objects.

The first object is to reduce costs and prevent the detachment of a wireless tag by printing the wireless tag on a target article.

The second object is to provide a wireless tag collective reading device. To collectively read closely arranged articles with wireless tags, this wireless tag collective reading device uses a driver such as a motor to apply radio waves, a magnetic field, or electromagnetic waves from a movable wireless tag reading antenna, and thereby electromagnetically reads the wireless tags. At the same time, the wireless tag collective reading device uses physical means or optical means or acoustic means such as ultrasonic waves to count the number of the articles with the wireless tags, and checks the number of the electromagnetically read wireless tags against the number of physically counted wireless tags. In this way, it is possible to instantaneously find out whether there is any error in reading by radio waves, or whether there is any broken wireless tag. When there is a trouble in a container that has the tag affixed thereto, buried therein or printed thereon, the wireless tag collective reading device easily locate this tag.

The third object is to provide a wireless tag collective reading device. This wireless tag collective reading device is structured to apply electromagnetic waves to a wireless tag located at a particular position alone. To this end, the setting of a circuit of a wireless tag reader/writer provided in the wireless tag collective reading device is artificially or automatically changed to change the application directivity, radiation intensity, and phase of radio waves or a magnetic field or electromagnetic waves applied to wireless tags. The position of a wireless tag reading antenna is also changed. Alternatively, closely arranged articles with wireless tags are placed in an anechoic chamber, and the articles are put one by one in and out of a radio wave or magnetic field or electromagnetic wave application region by mechanical means, so that the wireless tag collective reading device is structured to apply electromagnetic waves to a wireless tag located at a particular position alone. In this way, it is possible to ascertain whether the wireless tag is damaged, or ascertain which position of, for example, a rack the wireless tag is stored in when wireless tags are closely arranged in the rack.

The fourth object is to provide an article reading system. In order to ensure 100% traceability of an article from its production to use and disposal, the article reading system collectively manages, on a host server, information read from each wireless tag collective reading device. When a broken tag is found in the process, a new wireless tag is affixed at once, and a new ID is registered on the server to be linked with ID data for the wireless tag before broken. Alternatively, a wireless tag combined with a bar code is used. Thus, even when the wireless tag is broken or when no environment is available to read the wireless tag, the bar code is used to link the wireless tag ID data with the host server. In this way, the article reading system can ensure the traceability of the article in any situation or environment.

Solution to Problem

To achieve the above objects, a clustering method according to the present invention comprises the following aspects.

To achieve the above objects, a wireless tag according to this invention and its antenna are printed on the body of a container. The formation of a transistor circuit in a material other than silicon is under research and development using the technique for organic transistors. The formation on glass, a plastic such as polyethylene, or paper has already been achieved using, for example, an inkjet technique. According to the present invention, a wireless tag and its antenna circuit that use the above-mentioned technique are directly printed on the body or cap of a cap-equipped container such as a vacuum blood collection tube or a test tube.

The wireless tag is printed on the container or its cap, so that the detachment of the wireless tag when affixed as heretofore can be prevented. When the container is kept at an extremely low temperature, it is possible to avoid the problem of the breakage of an inlay (a wireless tag chip and an antenna mounted in a thin plastic sheet) of the affixed wireless tag caused by the application of slight stress or tension resulting from the curing of the inlay by the low temperature. As the wireless tag is formed on the container body by printing, the dielectric constants of substances constituting the container have a smaller influence, and stable reading is possible, as compared with a wireless tag that is buried in the cap of a container, the body of the container, or the bottom of the container. Moreover, as the wireless tag can be attached by printing simultaneously with the production of the container, the wireless tag does not need to be affixed later, and costs can be reduced. When the wireless tag is attached by printing, source tagging (attaching an individual ID to a tag) is conducted at the time of printing the wireless tag on the container. At the point where the wireless tag is printed, the ID of this tag is registered on a later-described host server by using a wireless tag collective reading device according to the present invention.

The wireless tag collective reading device according to this invention is not only advantageous to the above-mentioned wireless tag attached to the container by printing but also advantageous to both a wireless tag affixed to the body of a container with a seal and a wireless tag buried in, for example, a cap according to the conventional methods. Even when the above-mentioned containers are arranged and thus stored, the wireless tags can be collectively read in each storage rack without fail, and articles can be easily managed.

The wireless tag collective reading device according to this invention uses one or both of conventionally used radio waves and magnetic field to electromagnetically read the wireless tags. The wireless tag collective reading device also uses physical means or optical means or acoustic means such as ultrasonic waves to physically count the number of closely arranged containers, and checks the number of the electromagnetically read wireless tags against the number of physically counted wireless tags, thereby instantaneously detecting a reading error. This makes it possible to easily find out whether a wireless tag is damaged, locate the damage, find out the number of the containers with the wireless tags affixed thereto, and locate the containers with the damaged wireless tags affixed thereto.

In the wireless tag collective reading device according to this invention, a wireless tag reading antenna for reading the wireless tag printed on or affixed to the container is disposed around or above a rack, and is designed to be movable by a driver such as a motor. The wireless tag reading antenna disposed along the side of the rack uses the near-field (near region reading) technique, and is therefore disposed at the smallest distance from the rack and freely movable along the direction of the side of the rack by a driver such as a motor. The wireless tag reading antenna disposed above the rack is adjusted to be placed immediately above the highest container among the containers stored in the rack, and is movable on the rack by a driver such as a motor. This permits the wireless tag reading antenna to be as close to the wireless tag as possible.

The configuration described above is based on the assumption that the rack is fixed. Otherwise, the wireless tag reading antenna can be fixed, and the rack can be moved. Alternatively, both the rack and the wireless tag reading antenna may be configured to move. Another example of a possible way to move the rack is to place the rack on a table that is rotated by a driver such as a motor and surround the table by the wireless tag reading antennas. Alternatively, the surrounding wireless tag reading antennas may be fixed, and electromagnetic waves emitted from the wireless tag reading antennas may be electronically switched on or off freely in a software-operated manner. This allows the wireless tag reading antennas to behave as if moving.

The relation between the position of the rack and the position of the wireless tag reading antenna is changed to improve the reading accuracy of the affixed wireless tag in the rack. In general, the antenna of the wireless tag which is a conductor moves in the electric field or magnetic field such that induced electromotive force is generated in the antenna, and this induced electromotive force is used as a power source to drive the wireless tag and perform its function. Thus, the position of the wireless tag reading antenna and the position of the wireless tag can be successively changed to reinforce the induced electromotive force generated in the antenna of the wireless tag and improve the reading accuracy. By also using a method that intermittently applies the electromagnetic waves emitted by the wireless tag reading antenna, a phenomenon called "power sharing" that occurs when the electromagnetic waves are not equally applied to the closely arranged wireless tags can be avoided, and the wireless tags can be read more accurately.

The power sharing means a reading error that occurs when there are wireless tags located in the vicinity of one another, and one particular tag chip absorbs all the applied electromagnetic waves while a sufficient output of electromagnetic waves is not supplied to other tag chips.

When wireless tags of containers arranged in a rack are read by using one or both of radio waves and a magnetic field, reading by radio waves is used together with reading by a magnetic field because the containers may be closely arranged and the containers may contain water that absorbs electromagnetic waves. This is a technique called the near-field (near region reading) technique that is in wide use. The use of tags adapted to the near-field ensures that the wireless tags of the closely arranged containers containing water can be read without any particular processing of the wireless tags.

However, when the wireless tag is damaged, it is extremely difficult for conventional devices to find a container with the damaged wireless tag affixed thereto from among the closely arranged containers. As the antennas of the wireless tags affixed to the containers closely stored in the rack are in various directions, some of the antennas may not response well to the electromagnetic waves emitted from the wireless tag reading antenna. Moreover, when the total number of containers arranged and stored in the rack is always not fixed, it is necessary to visually count the number of containers rack by rack and check this number against the number of electromagnetically read containers in order to check the number of electromagnetically read containers against the actual number of containers. This leads to unrealistically considerable man-hour in operation.

Therefore, according to a function provided by the present invention, the number of containers is counted by a method that uses physical means or optical means or acoustic means such as ultrasonic waves to instantaneously check the number of electromagnetically read wireless tags against the actual number of containers. When there is a difference between the two numerical values, a warning is issued to indicate that there is a wireless tag that is damaged or that cannot be read, and the relevant container is located.

As the physical means for counting the number of containers, needle-like probes are erected on the bottom of the rack having the containers arranged therein. At the place where the container is put in the rack, the probe is depressed and switched on. At the place where no container is put in the rack, the probe is not depressed and therefore remains switched off. This may be used to count the number of probes that are switched on. In this case, one switch corresponds to one container in the rack, and the number of containers in the rack is instantaneously detected when the rack is stored in the wireless tag collective reading device.

As the optical means for counting the number of containers, optical switches are placed on the bottom of the rack having the containers arranged therein in the same pattern as the containers. Another way is to use means for moving, column by column or row by row, optical switches arranged along one column or one row of the rack. The switch is turned on when there is a container, and the switch remains off when there is no container. Accordingly, the number of switches that are turned on may be counted. As the optical switches, a combination of a light emitting portion and a light receiving portion of a light emitting diode may be used, or light receiving elements such as CdS cells may be arranged on the bottom of the rack in the same pattern as the containers. The brightness of the optical switch changes and the switched is turned on if there is a container on the upper surface. The switch remains off if the brightness does not change. This may be used to count the number of switches that are on.

As the acoustic means such as ultrasonic waves for counting the number of containers, combinations of ultrasonic transmitters and ultrasonic receivers may be arranged on the bottom of the rack having the containers arranged therein in the same pattern as the containers. Another way is to use means for moving, row by row or column by column, combinations of ultrasonic transmitters and ultrasonic receivers arranged in the same pattern as the containers along one column or one row of the rack. At the place where the container is put in the rack, the ultrasonic waves are reflected by the bottom of the container, and a signal thus enters the receiver. However, at the place where no container is put, no ultrasonic waves are reflected, and the switch remains off. This may be used to count the number of switches that are on.

According to the various methods described above, a microprocessor provided in the device compares the number of electromagnetically read wireless tags with the number of containers physically, optically or acoustically counted. If the number can be checked, that fact that all the containers are confirmed is displayed. If there is a reading error, a warning is displayed.

When there is a difference of checking results, an automatic reading device locates the wireless tag that cannot be read. The following three methods are conceivable to detect the position of a broken tag or a tag that does not respond due to unreached radio waves. The following three methods not only enable the detection of the position of a broken tag but also enable the acquisition of general information on the positions of the wireless tags of the containers closely arranged in the rack.

According to the first method, the intensity, directivity, and phase of radio waves or a magnetic field emitted from the wireless tag reading antenna are changed by properly setting the parameters of the circuit provided in the wireless tag reader/writer, such that the sensitivity of the wireless tag is intentionally changed place by place. In this way, the closely arranged wireless tags are inspected one by one, and judged to find out whether the wireless tags are normally readable. In this case, the automatic reading device uses the wireless tag reading antennas to conduct the inspection.

The wireless tag reader/writer incorporated in the wireless tag reading device has therein a mechanism for adjusting the intensity, phase, and angle of electromagnetic waves to be emitted. The phase, intensity, and angle of radio waves applied to the wireless tag can be freely changed via a phase modulation circuit, an intensity modulation circuit, and a radiation angle modulation circuit so that the radio waves can be output to any wireless tag reading antenna. The intensity, directivity, and phase of radio waves emitted from the antennas can be changed by giving proper instructions to the respective circuits, and a sensitive portion and an insensitive portion can be intentionally produced in a reading space. If the sensitive portion is moved by the instruction from the wireless tag reading device, sensitive reading electromagnetic waves can be applied to the wireless tags one by one. When there is a response, this means that the wireless tag at the relevant position is normal. When there is no response, this proves that the wireless tag at the relevant position is broken or that a response cannot be made due to the placement of the wireless tag or due to the improper direction of the antenna of the wireless tag at the time of collective reading.

According to the second method, a metal shield having a slit-shaped gap is disposed outside the rack in which containers are arranged. This metal shield is moved from one end of the rack to the other together with the wireless tag reading antenna to count the number of containers column by column or row by row. Four radio wave emitting antennas are arranged in the front and rear of the rack and on the left and right of the rack. All these antennas are structured to be laterally movable by a driver such as a motor. Initially, the two antennas arranged on the long sides of the rack are only used, and the two antennas arranged on the short sides are not used. A C-shaped metal shield plate is present outside the rack, and this metal shield plate has a gap corresponding to one column of rack. The antenna is placed in the rear of the gap of the metal shield, and the wireless tags are read column by column from one end of the rack to the other. In this case, the electromagnetic waves are emitted from the antenna by properly adjusting the mechanism for adjusting the intensity, phase, and angle of the electromagnetic waves emitted from the wireless tag reading device.

In contrast with the collective reading by electromagnetic wave emission, the intensity, directivity, and phase are changed to such a degree that a space corresponding to one column can be read. As the number of containers stored in the column being read is known in advance by the physical means, the electromagnetic reading result is checked against the physical reading result. If the figures add up, this proves that there is no reading error in this column. If the electromagnetic reading result is checked against the physical reading result and the counts do not match, this proves that there is a damaged wireless tag in this column or that there is a wireless tag that cannot be detected because its antenna is improperly placed.

The above-described method is then conducted for the short sides (rows) of the rack. If the place of the wireless tag that cannot be detected in the column of the rack is X and the place of the wireless tag that cannot be detected in the row of the rack is Y, it can be detected that the wireless tag located at coordinates (X, Y) has a problem.

According to the third method, the whole rack is placed in an anechoic zone, and the containers stored in the rack are taken out to a radio wave radiation region one by one via an actuator. After information in a wireless tag affixed to this container is read, the container is returned to the rack in the anechoic zone. Thus, all the containers in the rack are read one by one by radio waves or a magnetic field or electromagnetic waves, so that it is possible to judge whether the wireless tag is broken. From the position of the actuator, it is possible to also know at which position of the rack the wireless tag is stored. The space between the anechoic zone and the radio wave radiation zone is insulated from radio waves by an electromagnetic wave shielding cloth coated with a metal strip at given density. Alternatively, a hole equipped with an open/close mechanism such as a shutter is prepared in a metal plate, so that the hole is opened only when a container is taken out, and the hole is closed when electromagnetic waves are applied.

As described above, the wireless tag collective reading device according to the present invention can collectively read wireless tags affixed to containers that are closely stored in the rack. When there is a wireless tag that cannot be normally read due to the breakage of the wireless tag or the position of an antenna of the wireless tag affixed to the container, the wireless tag collective reading device can locate this wireless tag. The wireless tag collective reading device can also acquire information on the positions of the containers closely stored in the rack.

If there is an unreadable wireless tag, it is necessary to sort out problems as to whether the wireless tag affixed to the container is broken or whether the wireless tag is normal but the direction of its antenna during reading is improper. This can be easily determined by taking out this wireless tag and putting the wireless tag alone over an additionally provided wireless tag reading antenna for wireless tag breakage diagnosis at a short distance. When the wireless tag is judged to be unreadable due to its breakage, a new wireless tag is affixed to the container at once, and a new ID is thereby given to the container.

The wireless tag reading device according to the present invention sequentially sends reading results to the host server via the Internet, and the server stores the reading results on a database. In this way, the ID of the wireless tag read by the reading device is uniquely managed from the production of the container to the actual use and disposal of the container, and the traceability can be ensured. However, when a wireless tag is broken and a new wireless tag is affixed in the process as described above, a wireless tag ID that has heretofore been assigned at once is linked on the database in the server with the wireless tag ID affixed when the wireless tag is broken, so that 100% traceability can be ensured even when the wireless tag is broken.

Furthermore, a wireless tag combined with a bar code is affixed to a container. Thus, even when there is no wireless tag reading device on the distribution channel of the container, the bar code can be read instead. When the wireless tag breaks down on the distribution channel, 100% traceability can be ensured in any environment by the method that uses the bar code.

Advantageous Effects of Invention

The foregoing problems are solved by the present invention, and the following advantages can be expected.

Firstly, by printing the wireless tag on the container or its cap, the wireless tag does not need to be affixed to the container or its cap later, and costs can be reduced. Moreover, the wireless tag is not buried in the container or its cap, and there is thus no fear that the change in dielectric constant caused by the material of the container or its cap may affect the reading of the wireless tag. When the wireless tag is affixed to the container or its cap as heretofore, the wireless tag may be detached due to the change of the storage temperature of the container. Such concern is eliminated by printing the wireless tag on the container.

Secondly, in the wireless tag collective reading device according to the present invention, the wireless tag reading antenna is moved by a driver such as a motor. Alternatively, the wireless tag reading antennas are arranged around the rack. Otherwise, the position of the wireless tag reading antenna and the position of the wireless tag are changed relative to each other to read information in the wireless tag, or the phase, intensity, and direction of electromagnetic waves emitted from the wireless tag reading antenna are changed. This makes it possible to improve the accuracy of reading information in the wireless tags affixed to the clustered containers.

Thirdly, the use of the wireless tag collective automatic reading device according to the present invention eliminates much trouble that has heretofore been taken to visually count the number of containers stored in the rack, so that the number of containers can be instantaneously counted. Moreover, the numerical value obtained by collectively reading the wireless tags electromagnetically is checked against the number of containers obtained by using the physical means according to the present invention. This makes it possible to instantaneously know whether there is any wireless tag reading error or whether there is any broken wireless tag.

Fourthly, when the number obtained from electromagnetic reading results is checked against the number obtained by the physical means and there is a difference between the two numbers, the automatic reading device according to the present invention can be used to automatically specify the position of a wireless tag that is broken or that does not respond. This provides the advantage of saving the trouble of taking out the containers in the rack one by one and examining whether the wireless tags are readable.

Fifthly, the automatic reading device according to the present invention can be used to obtain information on the positions of the containers in the rack, and know at any time and manage the column and row of the rack where a desired container is stored.

Sixthly, when a container with a broken wireless tag affixed thereto is specified, a new wireless tag is affixed at once, and a new ID is given to the container, so that the article can be continuously managed after the wireless tag is broken.

Seventhly, by managing an article using a wireless tag together with a bar code, the article can be traced and managed even in an environment without any wireless tag reading device. When a wireless tag is broken, the article is managed by the bar code instead without affixing a new wireless tag, so that the article can be continuously managed.

Eighthly, the wireless tag collective automatic reading device, according to the present invention, stores reading results in a database on a server-side PC via the Internet. Since a conventional reading device is connected to a personal computer via a serial I/F such as RS-232C, one exclusive personal computer is needed for each reading device. Therefore, when there are more than one reading device, more than one personal computer are also needed, and much investment for equipment is needed. Moreover, as data collected by each reading device is stored in each personal computer in a dispersed manner, unified management of the data is impossible. However, the use of the device according to the present invention allows each reading device to send data to the database of one manager PC via an IP network. This enables the reduction of equipment to be introduced, the reduction of costs, unified management of data, and the prevention of the leakage of, for example, personal information.

Ninthly, the use of the present invention improves the traceability of an article. For example, when a blood sample is taken, the history of the process is preserved in the database of the center-side PC in regard to, for example, the kind and time of the examination, the sample test company that has conducted the examination, and the time of the disposal of the sample. This provides the advantage of preventing medical accidents and allowing details of the examination to be viewed at any time later. When the above-mentioned wireless tag is broken, a new tag is affixed to the broken wireless tag, and a newly given ID is linked with the prior ID on the server. Otherwise, a wireless tag combined with a bar code is used, so that when the wireless tag is broken, the bar code system is used instead, a bar code ID is linked with the prior ID on the server. This provides the advantage of traceability that can be ensured in any situation.

According to the present invention, it is possible to provide a clustering technique that permits a clustering-based DBSCAN algorithm to be sequentially performed and permits the reduction of costs for calculation to perform clustering in a situation where data is sequentially obtained.

BRIEF DESCRIPTION OF THE SEVERAL VIEWS OF THE DRAWING

FIG. 2 is a diagram showing an example of how a wireless tag that comprises an antenna and a wireless tag chip is printed on a container body according to one embodiment of the present invention;

FIG. 3 is a diagram showing an example of how a wireless tag is printed on a container bottom according to one embodiment of the present invention;

FIG. 4A is a diagram showing a configuration example of a rack and a container detecting device according to one embodiment of the present invention;

FIG. 4B is a diagram showing a configuration example of the rack and the container detecting device according to one embodiment of the present invention;

FIG. 4C is a diagram showing a configuration example of the rack and the container detecting device according to one embodiment of the present invention;

FIG. 12A is a top view showing the condition at the start of reading as the overview of a method of driving the container number reading unit shown in FIG. 11;

FIG. 12B is a perspective view showing the condition at the start of reading as the overview of the method of driving the container number reading unit shown in FIG. 11;

FIG. 13A is a top view showing the condition at the end of reading as the overview of the method of driving the container number reading unit shown in FIG. 11;

FIG. 13B is a perspective view showing the condition at the end of reading as the overview of the method of driving the container number reading unit shown in FIG. 11;

FIG. 14C is a side view in a short-side direction showing an example of the driving mechanism of the container number reading unit shown in FIG. 11;

FIG. 16A is a top view showing the configuration of a side antenna driving mechanism of a container collective reading device according to one embodiment of the present invention;

FIG. 16B is a side view in a long-side direction showing the configuration of the side antenna driving mechanism of the container collective reading device according to one embodiment of the present invention;

FIG. 19 is a top view showing another configuration example of the rack-stored container automatic reading device of the container collective reading device shown in FIG. 16A, FIG. 16B, and FIG. 16C;

FIG. 20A is a diagram showing an alternative configuration example of the rack-stored container automatic reading device of the container collective reading device shown in FIG. 16A, FIG. 16B, and FIG. 16C;

FIG. 20B is a diagram showing the alternative configuration example of the rack-stored container automatic reading device of the container collective reading device shown in FIG. 16A, FIG. 16B, and FIG. 16C;

FIG. 20C is a diagram showing the alternative configuration example of the rack-stored container automatic reading device of the container collective reading device shown in FIG. 16A, FIG. 16B, and FIG. 16C;

FIG. 21 is a block diagram showing internal processing of a controller of the automatic reading device;

FIG. 24 is a diagram showing a mechanism for applying electromagnetic waves to a particular wireless tag of the container;

FIG. 25A is a diagram showing a method of detecting a faulty wireless tag for each column of the rack;

FIG. 25B is a diagram showing the method of detecting a faulty wireless tag for each column of the rack;

FIG. 26 is a diagram showing another method of detecting a faulty wireless tag for each column of the rack;

FIG. 31B is a diagram showing the container position specifying operation;

FIG. 32 is a diagram showing another configuration example of an in-rack container position detecting mechanism;

FIG. 33A is a diagram showing an example of how to display rack-by-rack position detection information on a management PC;

FIG. 34 is a diagram showing a system overall configuration of an article management method that uses an IP network according to the present invention;

FIG. 35 is a diagram showing an example of how to ensure traceability by using a wireless tag according to the present invention in connection with an example of blood sample collection;

FIG. 36 is a diagram illustrating the embodiment of the present invention in connection with an example of a blood test process in a general clinic;

FIG. 37 is a diagram illustrating the embodiment of the present invention in connection with an example of a blood test process in a general clinic;

FIG. 38 is a diagram illustrating the embodiment of the present invention in connection with an example of a blood test process in a general clinic;

FIG. 39C is a diagram showing an example of a bar code label to be printed on and inlaid in a label surface of a wireless tag;

FIG. 39D is a diagram showing an example of a bar code to be printed on and inlaid in a label surface of a wireless tag;

FIG. 39E is a diagram showing an example of an adhesive tape (or a paste layer) when a bar code is printed on and inlaid in a label surface of a wireless tag; and FIG. 40 is a diagram showing an example of how to deal with a broken wireless tag.

DETAILED DESCRIPTION OF THE INVENTION

Hereinafter, an embodiment according to the present invention will be described in detail with reference to the drawings.

Figure 1A:
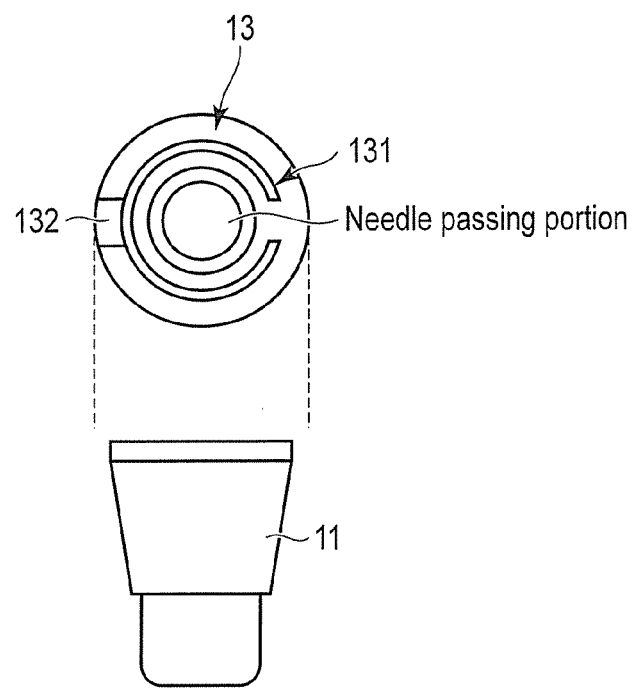
FIG. 1A is a diagram showing an example of how a wireless tag is printed on a container cap according to one embodiment of the present invention.
Figure 1B:
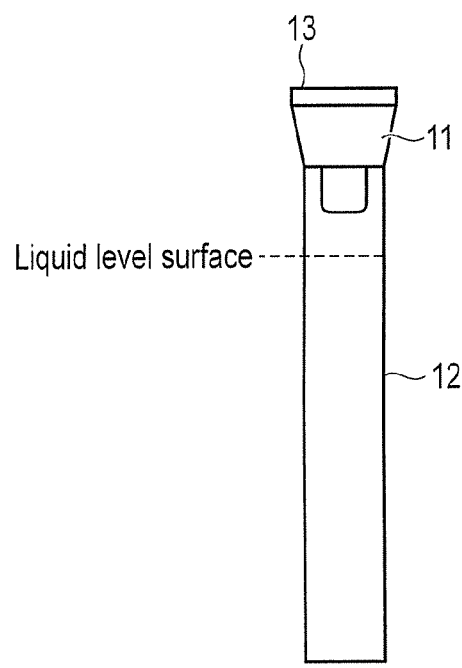
FIG. 1B is a diagram showing the example of how the wireless tag is printed on the container cap according to one embodiment of the present invention.

FIG. 1A shows a top view and a side view of an example of how a wireless tag is printed on a container cap 11 according to the present invention. FIG. 1B is side view showing how the container cap 11 is attached to a container body 12. When the present invention is used for a vacuum blood collection tube that is used in, for example, a blood test, a horseshoe-shaped loop antenna 131 and a wireless tag chip 132 connected to the antenna 131 are circumferentially printed on the upper surface of the container cap 11, and a wireless tag 13 is thereby formed on the upper surface of the container cap 11. This allows a through-hole for a blood collection needle to be made in the container cap 11 even when the wireless tag is printed and formed on the upper surface of the container cap 11.

FIG. 2 shows an example of how a wireless tag 15 that comprises an antenna 151 and a wireless tag chip 152 is printed on a container body 12 according to the present invention. The wireless tag 15 is not exclusively printed on the container body 12 in the longitudinal direction as shown in FIG. 2, and may be printed in the lateral direction. The length of the antenna 151 of the wireless tag 15 is calculated from the wavelength λ of electromagnetic waves applied to a wireless tag to be used, and determined by a method of printing on the container body 12.

FIG. 3 is a diagram showing an example of how a wireless tag is printed on the bottom of the container body 12 according to the present invention. A wireless tag 16 is printed on the bottom of the container 12. As in FIG. 1, the wireless tag 16 has a configuration in which a horseshoe-shaped loop antenna 161 is connected to a wireless tag chip 162.

FIG. 4A and FIG. 4B respectively show a container storage rack 21 in which containers 22 equipped with the wireless tags are stored and arranged, and the arrangement and configuration of a container detecting device 23. The container storage rack 21 has a predetermined matrix arrangement, and the container detecting device 23 has a configuration similar to that of the container storage rack 21. The container detecting device 23 is disposed under the container storage rack 21, so that the containers 22 actually put in the rack 21 can be detected and counted.

Figure 4D:
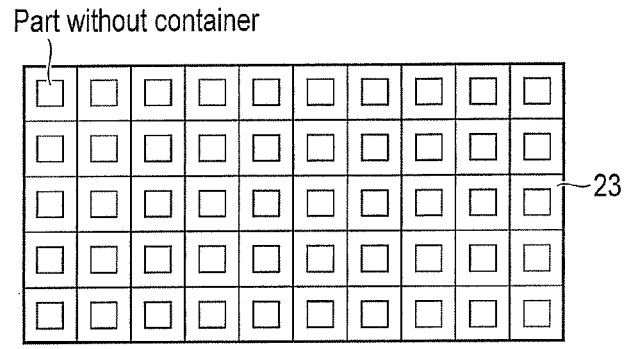
FIG. 4D is a diagram showing a configuration example of the rack and the container detecting device according to one embodiment of the present invention.

FIG. 4C shows a top view of the container storage rack 21 in which no containers 22 are put in some parts. When the container 22 is put in the rack 21, a sensor of the container detecting device 23 placed under the container 22 is invisible. However, at the place where no container 22 is put, the sensor of the container detecting device 23 is exposed. As shown in FIG. 4D, when there are no containers 22 stored in the container storage rack 21, the detection sensors of the container detecting devices 23 are arrayed on the bottom of the rack 21 in the same arrangement pattern as the containers 22.

Figure 5A:
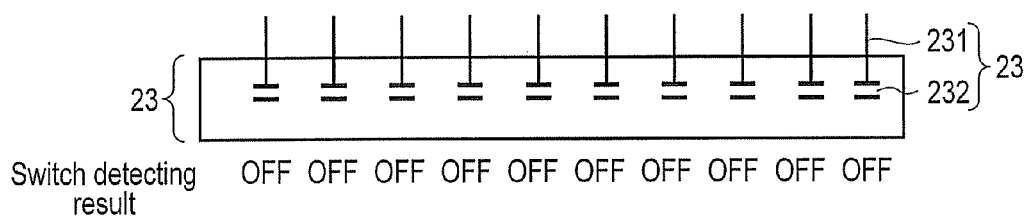
FIG. 5A is a diagram showing a specific example of the container detecting device shown in FIG. 4.
Figure 5B:
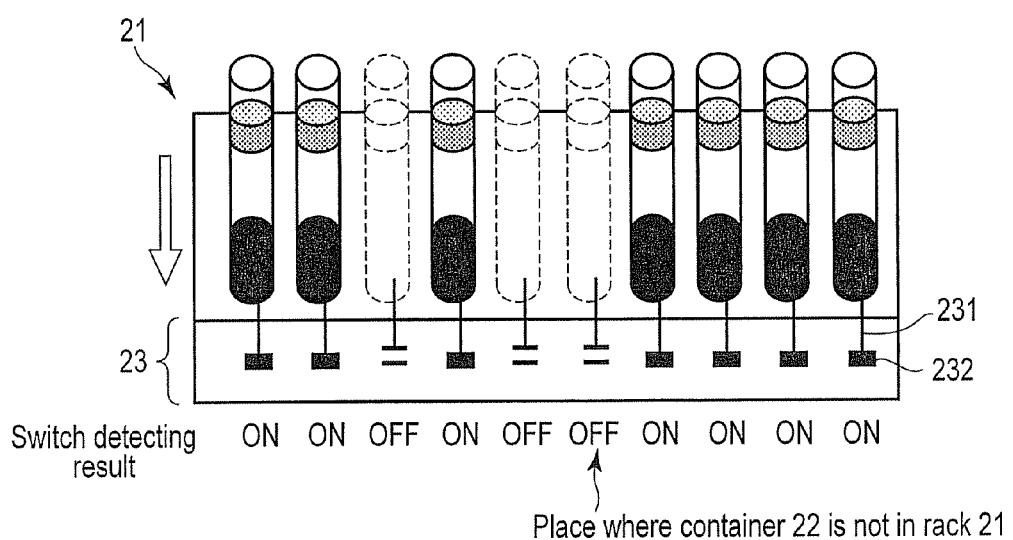
FIG. 5B is a diagram showing a specific example of the container detecting device shown in FIG. 4.

FIG. 5A and FIG. 5B show an arrangement structure when a probe-type detection sensor 231 is used as an example of the sensor for use in the container detecting device 23 according to the present invention. Although ten probe-type detection sensors 231 are shown in FIG. 5A and FIG. 5B, the sensors 231 are arranged in matrix form in accordance with the rack 21 for storing the containers 22. Now, if no container 22 is put in the rack 21, the probe-type detection sensor 231 has a probe 2311 lifted by a spring, and a switch 2312 is turned off.

Figure 6A:
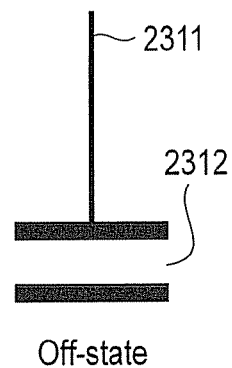
FIG. 6A is a diagram showing the configuration and operation of a container detecting device that uses a switch having physical contact as an example of the above-mentioned container detecting device.
Figure 6B:
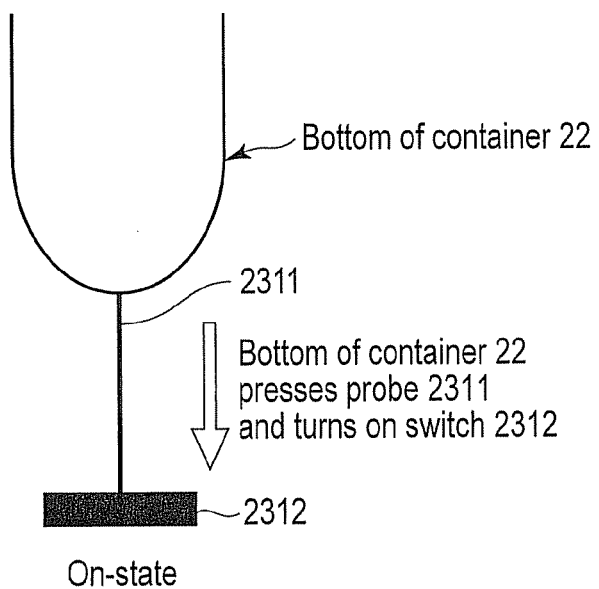
FIG. 6B is a diagram showing the configuration and operation of the container detecting device that uses the switch having physical contact as an example of the above-mentioned container detecting device.

FIG. 6A and FIG. 6B show the operation of the probe-type detection sensor 231 before the container 24 is put in the rack 21. At the place where the container 22 is present, the probe 2311 is depressed by the weight of the container 22, and the switch 2312 is turned off. However, at the place where no container is present, the probe 2311 is not depressed, and the switch 2312 remains off. Whether the container 22 is stored at each position of the rack 21 can be recognized by the two on- and off-states.

Figure 7A:
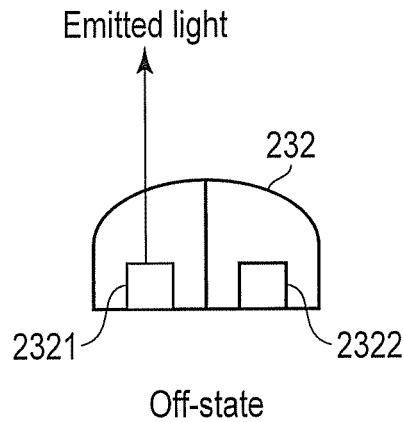
FIG. 7A is a diagram showing the configuration and operation of a container detecting device having a switch structure that uses an LED sensor as an example of the above-mentioned container detecting device.
Figure 7B:
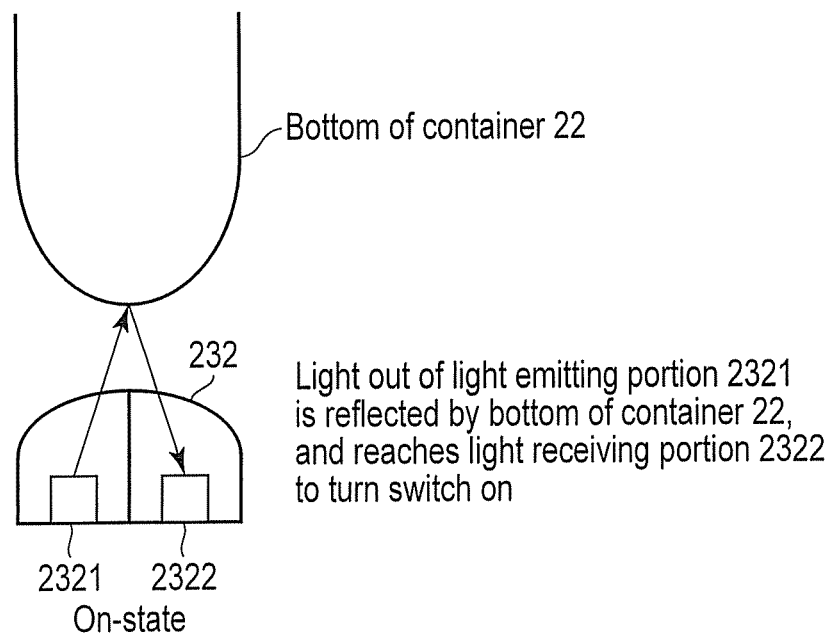
FIG. 7B is a diagram showing the configuration and operation of the container detecting device having the switch structure that uses the LED sensor as an example of the above-mentioned container detecting device.

FIG. 7A and FIG. 7B show the configuration and operation of the container detecting device 23 having a switch structure that uses an LED sensor 232. In the container detecting device 23 in this case, the LED sensor 232 is disposed under the place where each container 22 is disposed. This LED sensor 232 has an LED light emitting portion 2321 and a light receiving portion 2322 that are combined together, and is structured to emit light upward from the LED light emitting portion 2321 and be turned on by receiving the light reflected by the light receiving portion 2322. That is, when no container 22 is stored, the light emitted from the LED light emitting portion 2321 escapes upward and does not reach the light receiving portion 2322, and the LED sensor 232 remains off. However, when the container 22 is stored, the light from the LED light emitting portion 2321 is reflected by the bottom of the container 22 and reaches the light receiving portion 2322, and the LED sensor 232 is turned on. Whether the container is stored at each position of the rack can be recognized by the two on- and off-states. This is also possible if the LED sensor 232 is placed above the container 22 and the reflection from the container cap (not shown) is detected.

Figure 8A:
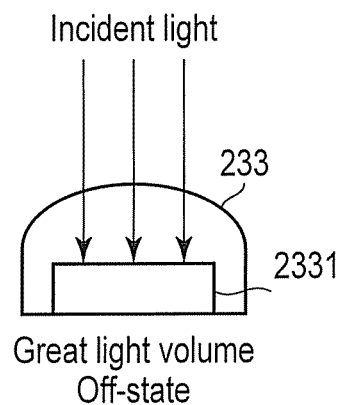
FIG. 8A is a diagram showing the configuration and operation of a container detecting device having a switch structure that uses a light volume sensor as an example of the above-mentioned container detecting device.
Figure 8B:
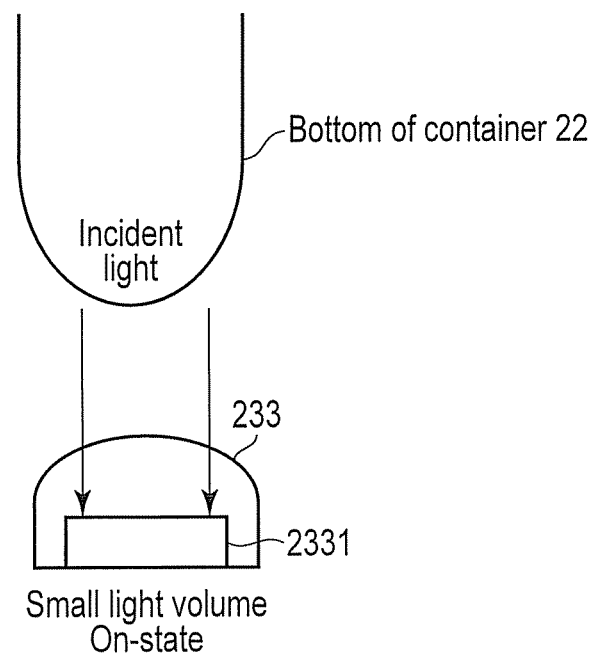
FIG. 8B is a diagram showing the configuration and operation of the container detecting device having the switch structure that uses the light volume sensor as an example of the above-mentioned container detecting device.

FIG. 8A and FIG. 8B show the configuration and operation of the container detecting device 23 having a switch structure that uses a light volume sensor 233 such as a CdS cell. In the container detecting device 23 in this case, the light volume sensor 233 is disposed under each container 22. This light volume sensor 233 is structured to be turned off when the volume of incident light is greater, and turned on otherwise.

When no container 22 is stored in the rack, the light volume sensor 233 detects a great volume of light, and is therefore turned off. When the container 22 is stored in the rack, the incident light is blocked by the container 22, and the light volume sensor 233 is therefore turned on. Whether the container 22 is stored at each position of the rack can be recognized by the two on- and off-states.

Figure 9A:
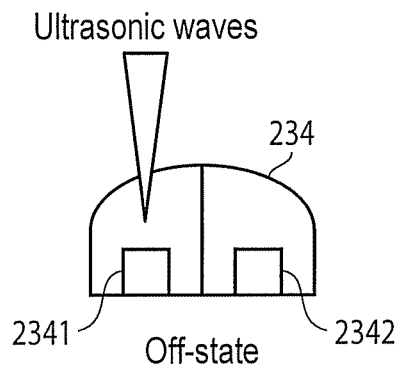
FIG. 9A is a diagram showing the configuration and operation of a container detecting device having a switch structure that uses an ultrasonic sensor as an example of the above-mentioned container detecting device.
Figure 9B:
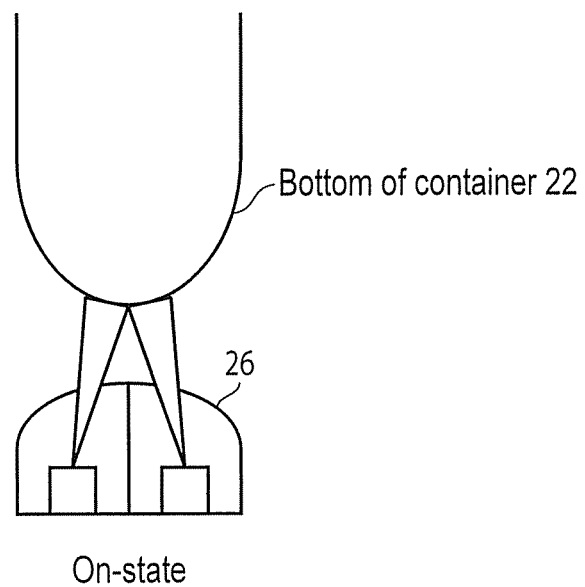
FIG. 9B is a diagram showing the configuration and operation of the container detecting device having the switch structure that uses the ultrasonic sensor as an example of the above-mentioned container detecting device.

FIG. 9A and FIG. 9B show the configuration and operation of the container detecting device 23 having a switch structure that uses an ultrasonic sensor 234. In the container detecting device 23 in this case, the ultrasonic sensor 234 is disposed under each container 22. This ultrasonic sensor 234 has an ultrasonic wave emission source 2341 and an ultrasonic wave receiving portion 2342 that are combined together, and is structured to emit ultrasonic waves upward from the ultrasonic wave emission source 2341 in the diagram and be turned on by receiving the reflected waves at the ultrasonic wave receiving portion 2342. That is, when no container 22 is in the rack, the ultrasonic waves are not blocked and thus travel straight, and cannot reach the ultrasonic wave receiving portion 2342, so that the ultrasonic sensor 234 is turned off. However, at the place where the container 22 is stored, the ultrasonic waves are reflected by the bottom of the container 22, and an ultrasonic signal enters the ultrasonic wave receiving portion 2342, so that the ultrasonic sensor 234 is turned on. Whether the container 22 is stored at each position of the rack can be recognized by the two on- and off-states.

Figure 10A:
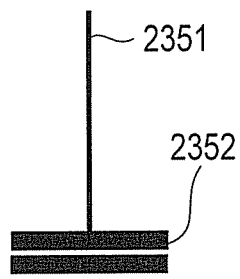
FIG. 10A is a diagram showing the configuration and operation of a container detecting device having a switch structure that uses a piezoelectric sensor as an example of the above-mentioned container detecting device.
Figure 10B:
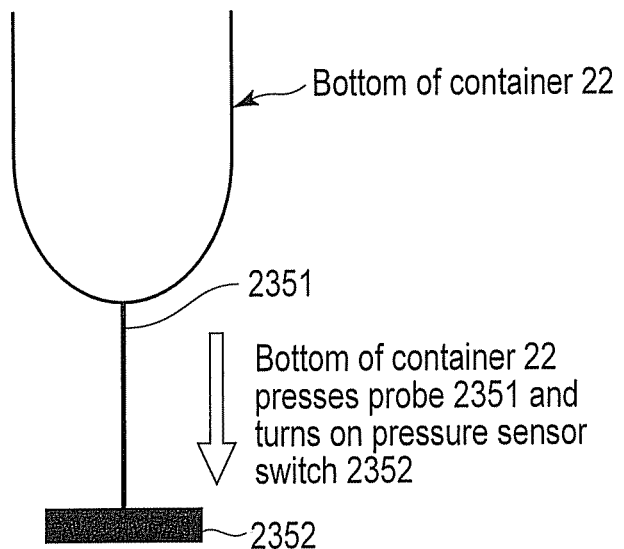
FIG. 10B is a diagram showing the configuration and operation of the container detecting device having the switch structure that uses the piezoelectric sensor as an example of the above-mentioned container detecting device.

FIG. 10A and FIG. 10B show the configuration and operation of the container detecting device 23 having a switch structure that uses a pressure sensor 235. In the container detecting device 23 in this case, the pressure sensor 235 is disposed under the place where each container 22 is disposed. This pressure sensor 235 has a probe 2351 extending upward in the diagram and a piezoelectric switch 2352 that are combined together, and is structured so that the piezoelectric switch 2352 is turned on by pressure applied downward to the probe 2351. That is, when no container 22 is put in the rack 21, nothing is in contact with the probe 2351, so that no pressure is applied to the piezoelectric switch 2352, and the pressure sensor 235 remains off. However, when the container 22 is put in the rack 21, the container 22 presses the probe 2351, and the piezoelectric switch 2352 is turned on accordingly.

Each of the sensors described above may be disposed on the bottom of the rack or above the rack. The sensors may be arranged in accordance with the storage pattern of the rack, or the sensors arranged in one row or column of the rack may be moved column by column or row by row and thereby scanned. For example, when the rack has five columns and ten rows, the sensors may be arranged in five columns and ten rows. Alternatively, the sensors in five columns may be moved row by row ten times and thereby scanned, or the sensors in ten rows may be moved column by column five times and thereby scanned.

Figure 11:
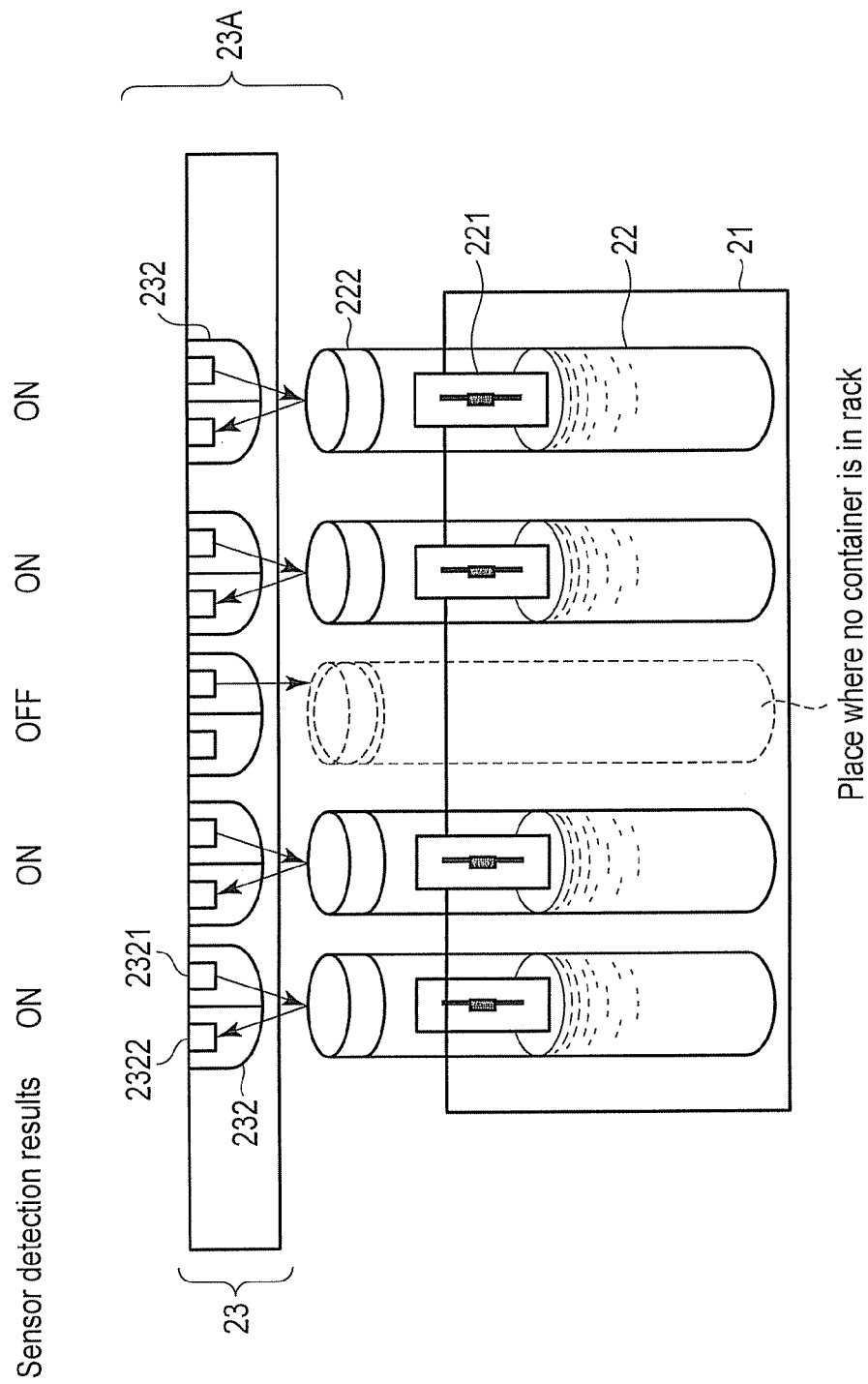
FIG. 11 is a diagram showing a configuration example of a container number reading unit that uses an LED as an example of the above-mentioned container detecting device.

FIG. 11 shows a configuration example of a container number reading unit 23A that uses an LED. In this example, the container number reading unit 23A having the LED light receiving sensor units (hereinafter, LED sensors) 232 linearly arranged along the column of the rack 21 is moved column by column in the rack 21 and thereby performs a scan to count the number of the containers 22. The container number reading unit 23A moves while sensing the top of the rack 21 row by row. The sensor 232 at the place where no container 22 is stored is not turned on because there is no reflection by a container cap 222. For example, when the rack has five rows and ten columns, the container number reading unit 23A having five sensors 232 arranged in a column can be moved ten times to count the number of all the containers 22 in the rack 21.

FIG. 12A and FIG. 12B show the overview of an actual method of driving the container number reading unit 23A shown in FIG. 11, and show the condition at the start of reading. FIG. 13A and FIG. 13B show the condition of the container number reading unit 23A at the end of reading. The container number reading unit 23A is disposed above the rack 21, and its pillars 23B are laterally moved to scan the top of the rack 21 and count the containers 22 in the rack 21. Although the container number reading unit 23A is moved above the rack 21 in this case, the container number reading unit 23A may otherwise be fixed and read by moving the rack 21.

Figure 14A:
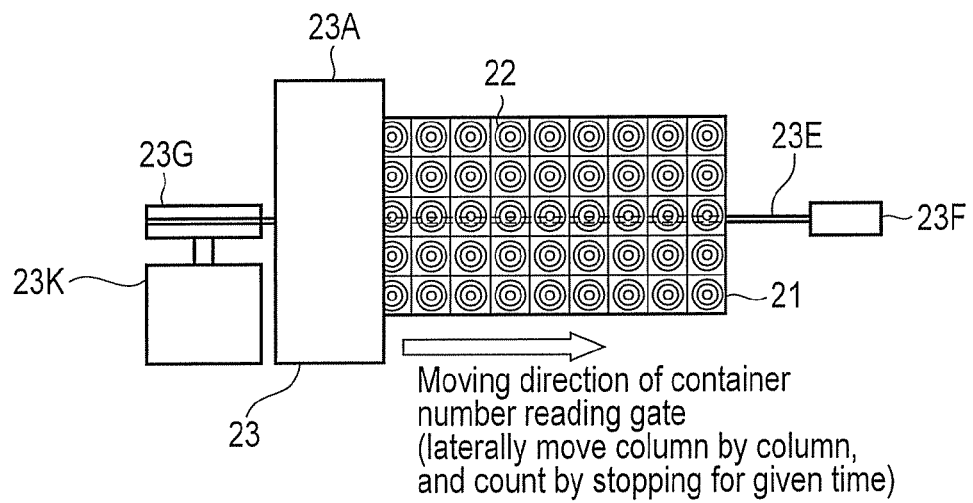
FIG. 14A is a top view showing an example of a driving mechanism of the container number reading unit shown in FIG. 11.
Figure 14B:
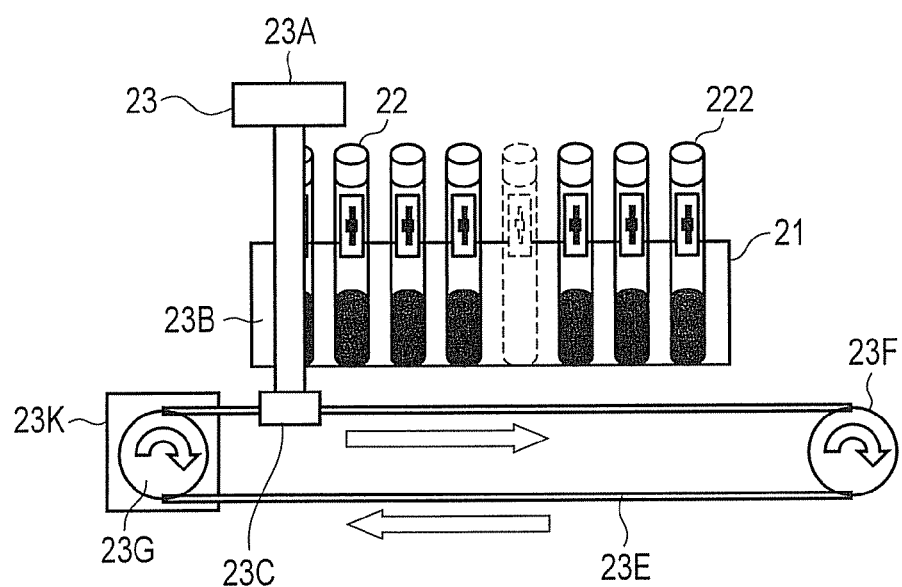
FIG. 14B is a side view in a long-side direction showing an example of the driving mechanism of the container number reading unit shown in FIG. 11.

FIG. 14A, FIG. 14B, and FIG. 14C show an example of a driving mechanism of the container number reading unit shown in FIG. 11. The container number reading unit 23A is disposed above the rack 21 by the pillars 23B. The pillars 23B are fixed to a number reading gate moving table 23C. The moving table 23C is fixed to a chain (or belt) 23E. The chain 23E is configured to be movable laterally in the diagram by a motor 23D and the gate moving table chain (or belt) 23E through rotation gears 23F and 23G. A stepping motor is used as the motor 23D, and the motor 23D is configured to accurately move the moving table 23C to the next column or row after the containers 22 in one row or column of the rack is counted.

Figure 15:
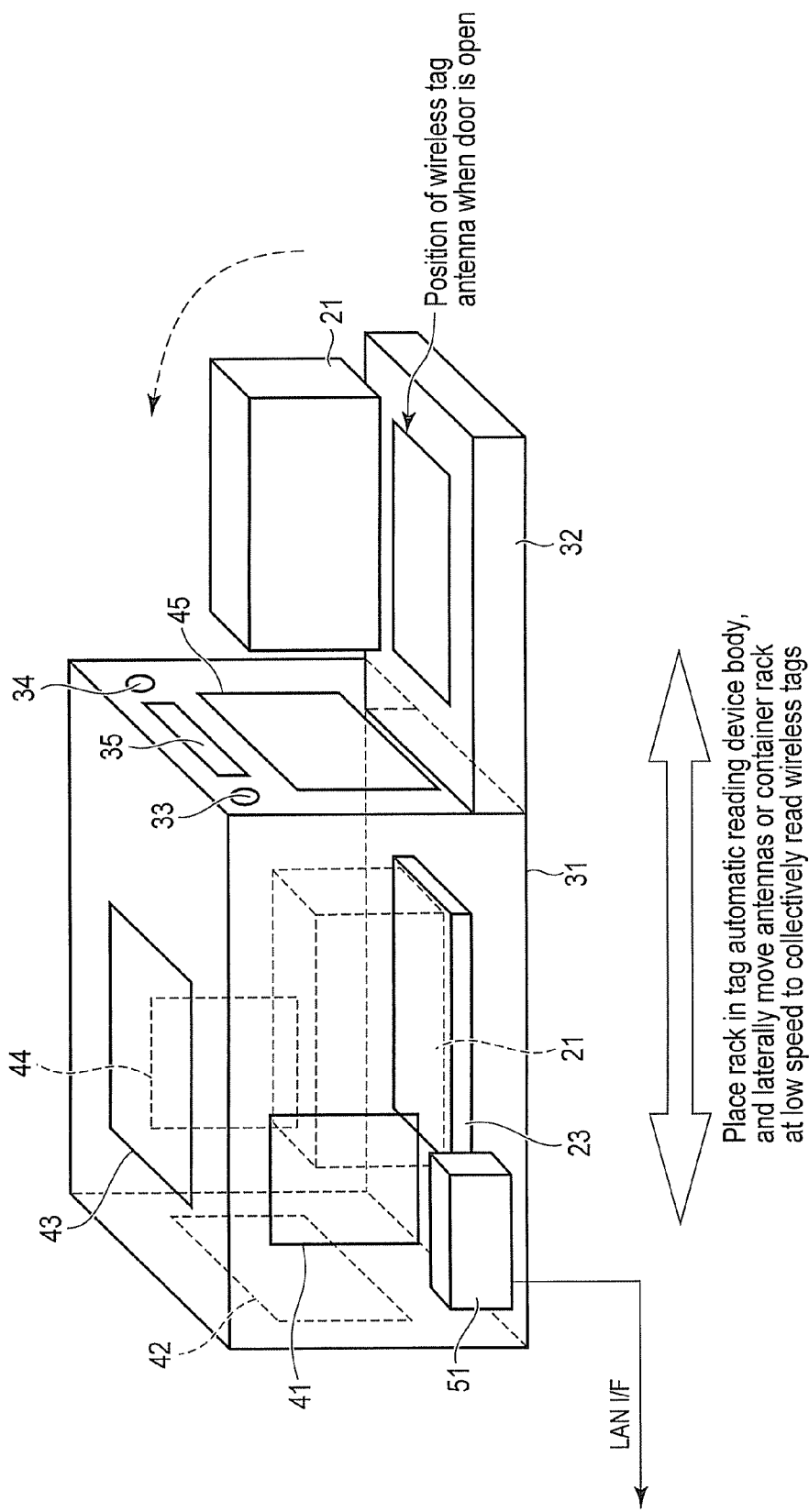
FIG. 15 is a perspective view showing the overview of a rack-stored container automatic reading device using the above-mentioned container detecting device.

FIG. 15 shows an example of a wireless tag collective reading device for the containers 22 stored in the rack according to the present invention. The wireless tag collective reading device according to the present invention is not only applicable to the printed wireless tag described above but also applicable to a normal wireless tag, a wireless tag buried in a container, and a wireless tag affixed to a container.

In FIG. 15, a reading device 31 is box-shaped, and is provided with a door 32 for putting in and out the container rack 21. This door 32 is also equipped with a wireless tag reading antenna 45. In the reading device 31, wireless tag reading antennas 41 to 45 are arranged in the front and rear of the storage rack 21, on the left and right of the storage rack 21, and above the storage rack 21. The above-described container detecting device 23 is installed under the storage rack 21. When the containers 21 are placed in the reading device 31, the container detecting device 23 immediately counts the number of the containers stored in the rack 21. There are four ways to read the wireless tags. The first way is to use a driver such as a motor to move the wireless tag reading antenna along the side of the rack 21. The antenna moves from one end of the rack 21 to the other, and thereby collectively reads the wireless tags of the containers 21.

The second way is to fix the antenna and use a driver such as a motor to move the storage rack 21 so that the storage rack 21 passes in front of the antenna, thereby collectively reading the wireless tags of the containers 22. The third way is to fix the wireless tag reading antennas and use a driver such as a motor to rotate the rack 21 on a turntable. The fourth way is to fix the rack 21 on a table and emit electromagnetic waves simultaneously or in turn from the wireless tag reading antennas surrounding the rack 21 to collectively read the wireless tags.

In the reading device 31, the number of the electromagnetically read wireless tags and the number of the containers counted by the container detecting device 23 are displayed on a reading result display 35, and an arrangement plan of the containers 22 in the rack 21 is also displayed at the same time. If the two values are checked against each other and found to be different, a warning is issued, and an indication for an abnormality is shown, and then a lamp 34 is turned on. If the values correspond to each other as a result of the check, an indication for a normal termination is shown, and a lamp 33 is turned on, and then data such as IDs stored in the wireless tags is sent to the host server from a device controller 51 via a network. If the wireless tags of the containers 22 stored in the rack 21 are normally read, the door 32 is opened to take out the rack 21, and a next rack is stored.

Figure 16C:
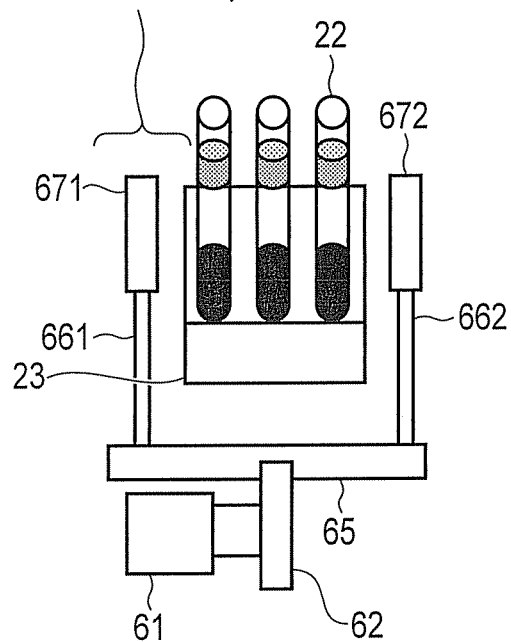
FIG. 16C is a side view in a short-side direction showing the configuration of the side antenna driving mechanism of the container collective reading device according to one embodiment of the present invention.

FIG. 16A, FIG. 16B, and FIG. 16C show the structure of a driving mechanism of a side wireless tag reading antenna in the wireless tag collective reading device according to the present invention. Wireless tag reading antennas 671 and 672 arranged along the sides are fixed to a wireless tag reading antenna moving table 65 by pillars 661 and 662. The wireless tag reading antennas 671 and 672 arranged along the sides are symmetrically located, and the reading antenna moving table 65 moves the two antennas. The reading antenna moving table 65 is equipped with a chain or belt 64, and is configured to be freely movable laterally via rotation gears 62 and 63. A motor 61 for moving the wireless tag reading antenna moving table 65 is disposed in one of the rotation gears. In order to collectively read the wireless tags printed on or affixed to the containers 22 in the rack 21, the reading antenna moving table 65 disposed along the side is moved from the left end of the rack 21 to the right end, and then once stopped, and further moved from the right end to the left end, thereby making a to-and-fro motion. The accuracy of electromagnetic reading is effectively improved if the antennas are moved back and forth several times to read wireless tag information.

Figure 17A:
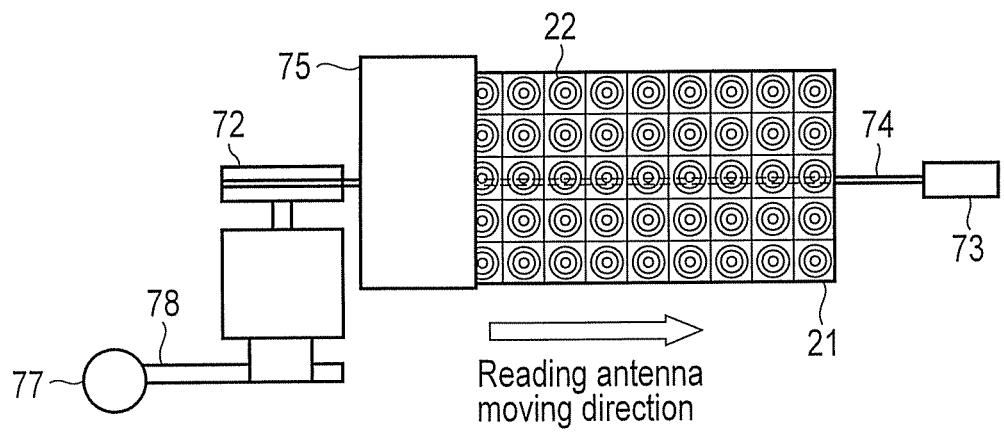
FIG. 17A is a top view showing an upper antenna driving mechanism of the container collective reading device shown in FIG. 16A, FIG. 16B, and FIG. 16C.
Figure 17B:
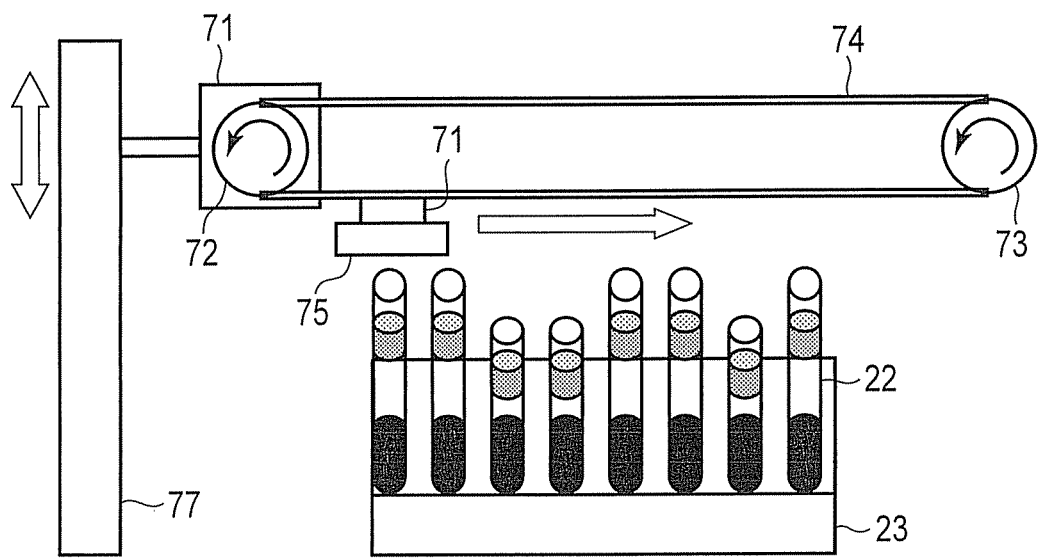
FIG. 17B is a side view in a long-side direction showing the upper antenna driving mechanism of the container collective reading device shown in FIG. 16A, FIG. 16B, and FIG. 16C.
Figure 17C:
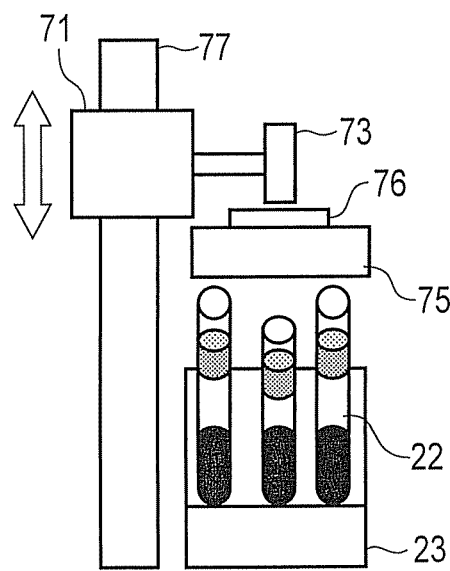
FIG. 17C is a side view in a short-side direction showing the upper antenna driving mechanism of the container collective reading device shown in FIG. 16A, FIG. 16B, and FIG. 16C.

FIG. 17A, FIG. 17B, and FIG. 17C show a driving mechanism of an upper wireless tag reading antenna 75 of the wireless tag collective reading device according to the present invention. The upper wireless tag reading antenna 75 is connected to a wireless tag reading antenna moving table 76. The wireless tag reading antenna moving table 76 is equipped with a chain or belt 74, and is configured to be laterally movable via rotation gears 72 and 73. One of the right and left rotation gears is equipped with a motor 71 for moving the upper wireless tag reading antenna 75. As the containers 22 may conceivably vary in height, the wireless tag collective reading device according to the present invention allows the height of the upper wireless tag reading antenna 75 to be set immediately above the highest container. Thus, the wireless tag reading antenna 75 can be set at the highest position and read when the rack 21 has containers that vary in height, and the antenna can be set at a low position when all the containers 22 are low. Therefore, the upper wireless tag reading antenna 75 can be brought as close to the wireless tags as possible.

Figure 18A:
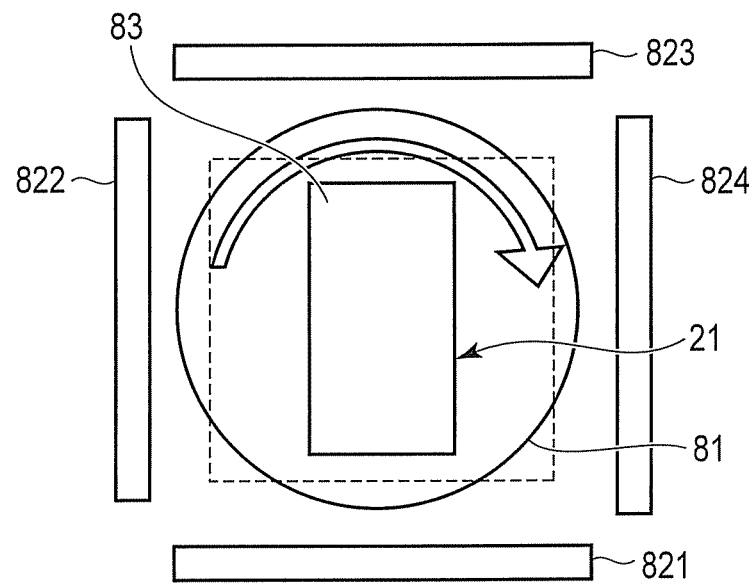
FIG. 18A is a top view showing the overview of a rack-stored container automatic reading device of the container collective reading device shown in FIG. 16A, FIG. 16B, and FIG. 16C.
Figure 18B:
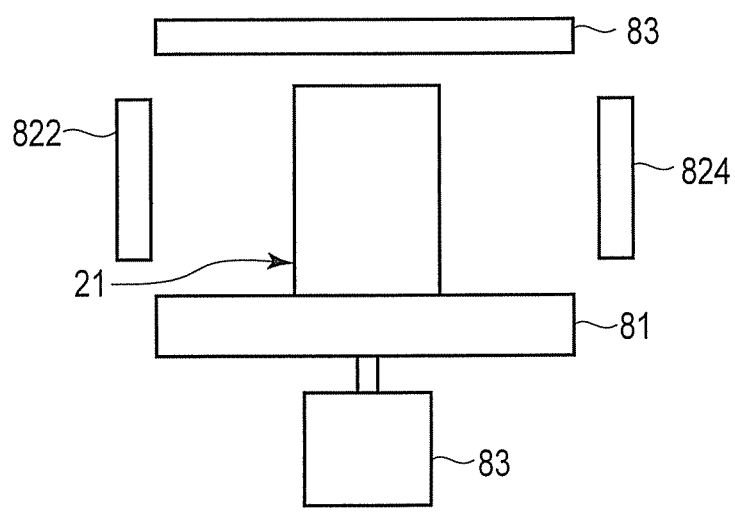
FIG. 18B is a side view showing the overview of the rack-stored container automatic reading device of the container collective reading device shown in FIG. 16A, FIG. 16B, and FIG. 16C.

FIG. 18A and FIG. 18B show another example of the relative arrangement of antennas and the rack in the wireless tag collective automatic reading device according to the present invention. In FIG. 15, FIG. 16A, FIG. 16B, FIG. 16C, FIG. 17A, FIG. 17B, and FIG. 17C, the antenna or the rack moves back and forth on a straight line to perform collective reading. In the structure shown in FIG. 18A and FIG. 18B, the rack 21 is placed on a rotary rack storage turntable 81 around which wireless tag reading antennas 821 to 824 are arranged. The container detecting device 23 is disposed under the rack 21. In this condition, the rack 21 is placed on the turntable 81. A motor 83 for rotating the turntable 81 is disposed under the turntable 81, and the turntable 81 is rotated several times to collectively read the wireless tags of the containers 22. A wireless tag reading antenna 83 is also disposed above the rack 21, and can change its attachment position in the height direction as shown in FIG. 17A, FIG. 17B, and FIG. 17C. For low containers, the antenna is set at a low position to be as close to the wireless tags as possible.

In this form, the antennas are disposed around the turntable 81 and also under or above the rack 21 to improve the reading accuracy. The container detecting device 23 is disposed above or under the rack 21, and simultaneously counts the number of the containers 22.

FIG. 19 shows another example of the relative arrangement of antennas and the rack in the wireless tag collective automatic reading device according to the present invention. In FIG. 18A and FIG. 18B, the wireless tag reading antennas arranged around the turntable 81 are fixed. In the present device, a container storage rack mounting table 91 and the rack 21 disposed thereon are fixed, and wireless tag reading antennas 921 to 928 are arranged around the mounting table 91, thereby enabling collective reading.

Electromagnetic waves from the wireless tag reading antennas may be emitted all at once or emitted in turn to draw a circle, or a pair of opposite antennas alone may emit electromagnetic waves. In short, the emission of radio waves is varied depending on the condition during collective reading to improve the reading accuracy. In this form as well, an additional wireless tag reading antenna is disposed above or under the rack, and the container detecting device 23 is disposed above or under the rack 21.

As an advanced feature according to this form, reading is performed more than one time by changing the intensity, directivity, and phase of the electromagnetic waves emitted from the antennas, the number of the emission antennas, and the radiation angle of the radio waves in accordance with a principle similar to that of a CT scanner in medical equipment. Accordingly, the position of the wireless tag that is broken or that does not respond is detected.

FIG. 20A, FIG. 20B, and FIG. 20C show another example of a container detecting method according to the present invention that uses optical means. In these drawings, the wireless tag reading antenna is not shown. The container detecting device 23 is disposed under the container storage rack 21, and the number of containers in the rack 21 is counted. At the same time, a camera A1 is set over the upper surface of the rack 21, and photographs the whole upper surface of the rack. An image processor A2 comprising a processor unit equipped with an image recognition engine is connected to the camera A1. The image processor A2 processes images, and specify the position where no container is present. This can be checked against the result obtained by the container detecting device 23 to more accurately specify the position where no container is present. It should be understood that whether a container is present may be detected by the container detecting device alone or the camera alone.

FIG. 21 shows a block diagram of a device for checking the number of containers in the storage rack against the number of containers electromagnetically read by wireless tag reading antennas. Wireless tag reading antennas B11 to B1n are connected to the wireless tag reading device. These antennas are arranged at various places as shown in FIG. 18A, FIG. 18B, FIG. 19, FIG. 20A, FIG. 20B, and FIG. 20C. On the other hand, the container detecting device 23 counts the number of containers stored in the rack by the physical means, optical means, or acoustic means in accordance with the methods described above. The two pieces of information are checked against each other by a microprocessor B4 to check the number of electromagnetically read wireless tags against the number of the containers counted by the container detecting device 23. If the two numbers correspond to each other, a green lamp is turned on to indicate on a display B5 that the processing is normal, and then data is sent to the host server computer via a network. If the difference between the reading numbers is found as a result of the check, a red lamp is turned on to issue a warning, and this fact is indicated on the display B5. Further, reading is again performed, or a faulty point is specified. The positions of the containers in the rack are displayed on the display.

Figure 22:
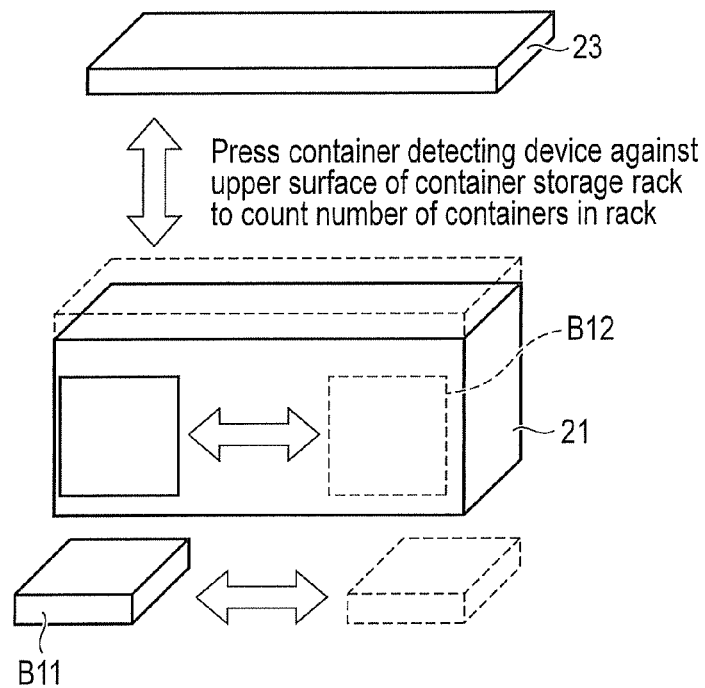
FIG. 22 is a diagram showing an overview of a method of reading a wireless tag on the bottom of the container.

FIG. 22 shows an example of a collective reading method when the printed wireless tag according to the present invention is printed on the bottom of the container. The containers 22 having wireless tags printed on the bottom are stored in the rack 21. The wireless tag reading antenna B11 disposed under the rack 21 is moved under the rack to collectively read the wireless tags. The container detecting device 23 is put on the rack to count the number of the containers 22 by the physical means, optical means, or acoustic means. Although the wireless tag reading antenna is only shown at one place under the rack in FIG. 22, an auxiliary antenna B12 can be placed, for example, on the side surface of the rack.

Figure 23:
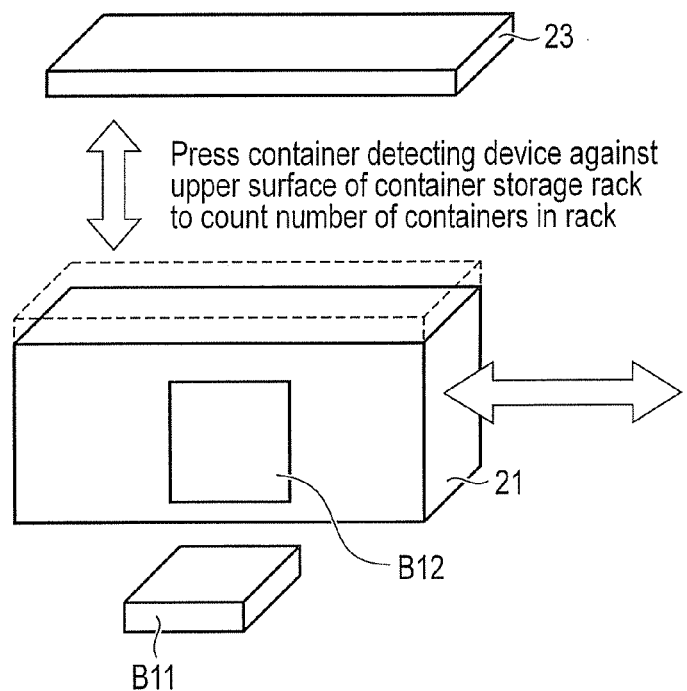
FIG. 23 is a diagram showing another overview of the method of reading the wireless tag on the bottom of the container.

FIG. 23 is substantially the same as FIG. 22 in that the wireless tag reading antenna 311 is fixed, and is only different from FIG. 22 in that the rack 21 moves over the antenna B11.

FIG. 24 shows how the position of a wireless tag that cannot be read by the electromagnetic waves emitted from the wireless tag reading antennas B11 to B1n is specified by properly changing the setting of an internal circuit of a wireless tag reader/writer 36 incorporated in the wireless tag collective reading device according to the present invention to adjust, for example, the phase, intensity, and angle of the emitted electromagnetic waves. When there is a difference between the electromagnetic reading and the physical reading that are checked against each other, the microprocessor B4 sends a command to the wireless tag reader/writer B6 incorporated in the wireless tag collective reading device. The wireless tag reader/writer B6 has therein a phase modulation circuit B62, an intensity modulation circuit B63, and a radiation range changing circuit B64, and the phase, intensity, and angle of the electromagnetic waves emitted from the wireless tag reading antennas B11 to B1n can be freely changed in accordance with the command from the microprocessor B4. The wireless tag reader/writer B6 also has a switching device B61 for the emission antennas B11 to B1n, and it is thus possible to determine which antenna to emit electromagnetic waves in accordance with the command from the microprocessor B4.

FIG. 25A and FIG. 25B show an example of a method of detecting a faulty or broken wireless tag in the rack or a wireless tag that does not respond to electromagnetic waves due to arrangement conditions such as the direction of the antenna. The phase and intensity of the electromagnetic waves emitted by the wireless tag reading antennas B11 and B12 can be changed by the near-field technique. The phase and intensity of the opposite antennas can be adjusted to only specify a particular column or row of the rack 21 to be a reading range. The phase and intensity are changed in this condition, and, for example, if five containers are in one column, the position of sensitivity Q for wireless tag reading is moved from the first container to the fifth container, the containers can be read and inspected one by one. The number of containers in the relevant column has been counted by the container detecting circuit described above. Therefore, the container that does not respond to the emitted radio waves can be specified.

FIG. 26 shows another example of a method of detecting a faulty or broken wireless tag in the rack or a wireless tag that does not respond to electromagnetic waves due to arrangement conditions such as the direction of the antenna. In this case, metal shield plates B71 and B72 are disposed in front of the opposite wireless tag reading antennas B11 and B12, and each of the shield plates is provided with a space corresponding to one column (or one row) of containers. The reading electromagnetic waves emitted from the wireless tag reading antennas B11 and B12 radiate through these spaces alone. In this way, the actual number of the containers 22 is checked against the read number column by column, and a wireless tag that does not respond is found in the column for which the figures do not add up. The same operation is performed for one row of containers, and the broken wireless tag can be specified from the column (X) and the row (Y).

Figure 27:
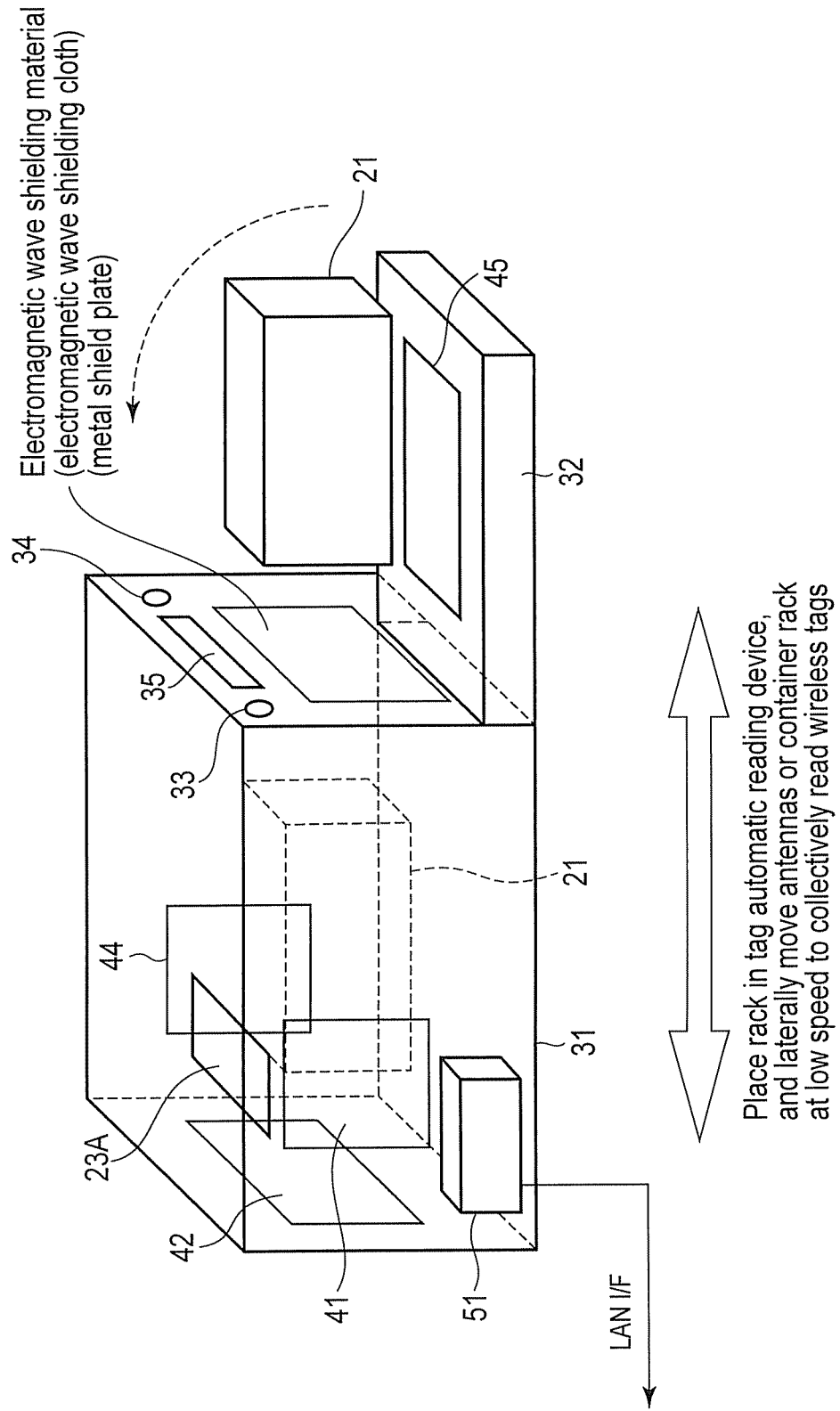
FIG. 27 is a perspective view showing an example of a wireless tag collective automatic reading device that uses a gate-type container number reading unit.

FIG. 27 shows a box-shaped reading device similar to that shown in FIG. 15, and this example uses the gate-type container number reading unit 23A shown in FIG. 12A, FIG. 12B, FIG. 13A, FIG. 13B, FIG. 14A, FIG. 14B, and FIG. 14C. In this case, the wireless tag reading antenna 43 over the upper surface of the container shown in FIG. 15 is mounted, and the container number reading unit 23A and an electromagnetic wave shielding material (e.g., an electromagnetic wave shielding cloth or a metal shield plate) are placed instead.

Figure 28A:
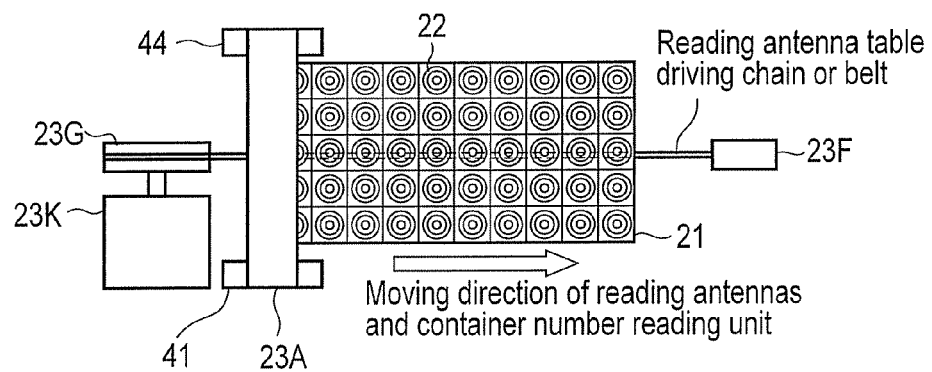
FIG. 28A is a top view showing a driving mechanism antennas and a container number reading unit when the gate-type container number reading unit is used.
Figure 28B:
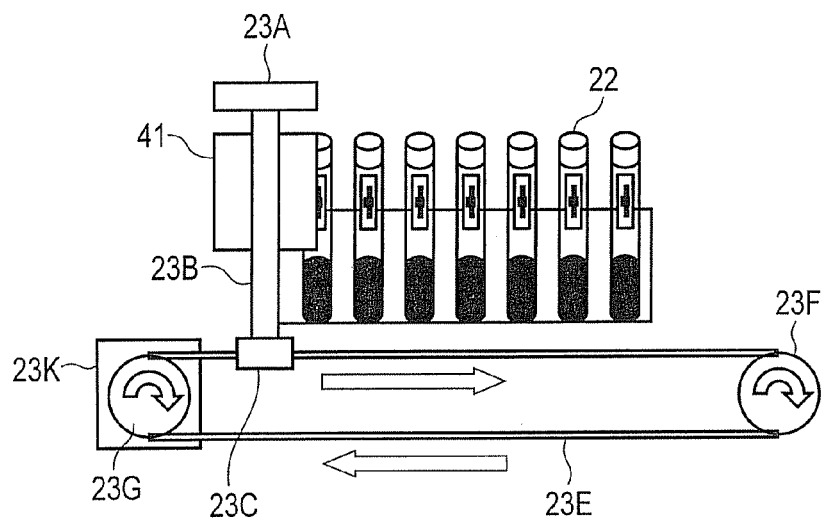
FIG. 28B is a side view in a long-side direction showing the driving mechanism of the antennas and the container number reading unit when the gate-type container number reading unit is used.
Figure 28C:
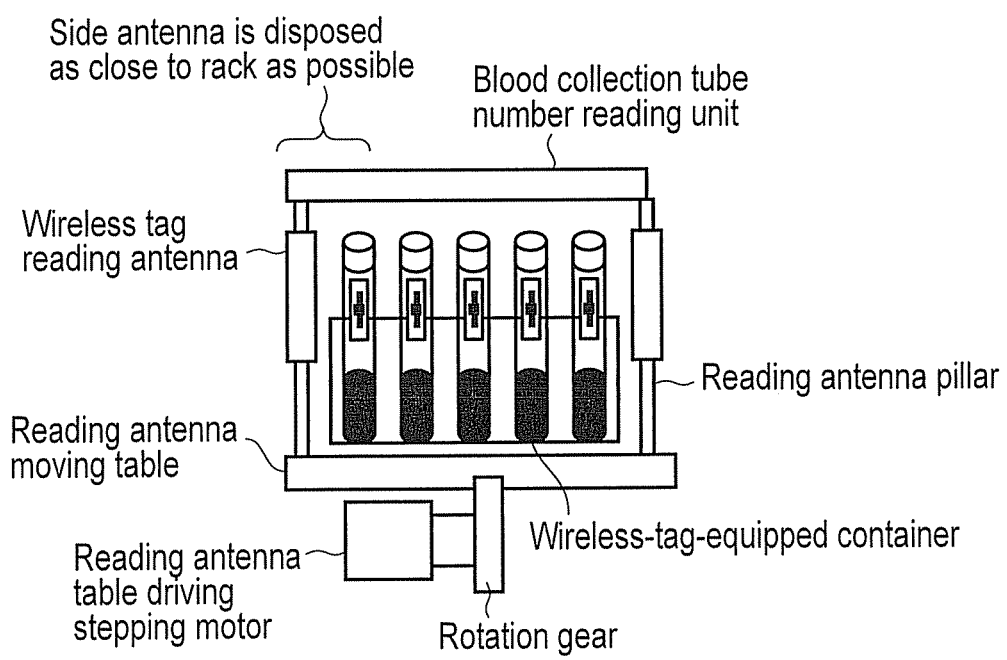
FIG. 28C is a side view in a short-side direction showing the driving mechanism of the antennas and the container number reading unit when the gate-type container number reading unit is used.

FIG. 28A, FIG. 28B, and FIG. 28C show a box-shaped reading device similar to that shown in FIG. 15. The gate-type container number reading unit 23A shown in FIG. 12A, FIG. 12B, FIG. 13A, FIG. 13B, FIG. 14A, FIG. 14B, and FIG. 14C is used. A driving mechanism of antennas 41 and 44 and the container number reading unit 23A in this case is shown. The side wireless tag reading antennas 41 and 44 are mounted on the gate pillars 23B of the container number reading unit 23A. The reading unit 23A and the antennas 41 and 44 are simultaneously moved to physically ascertain the number of containers and electromagnetically read the wireless tags.

Figures 29A, 29B:
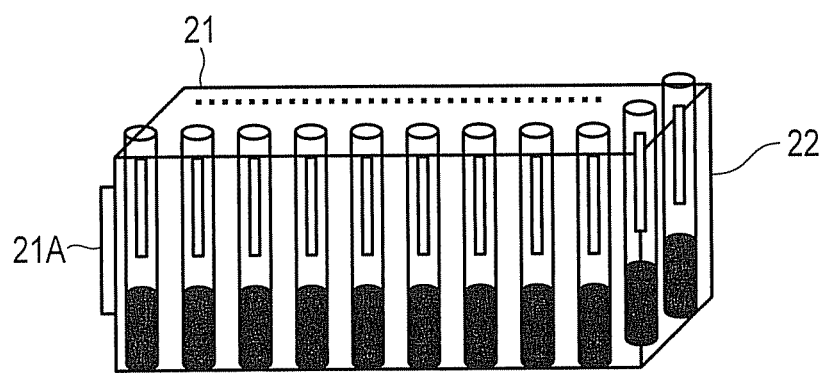
FIG. 29A is a top view showing an example of the position detection of each container stored in the rack.
FIG. 29B is a perspective view showing an example of the position detection of each container stored in the rack.
Figure 29C:
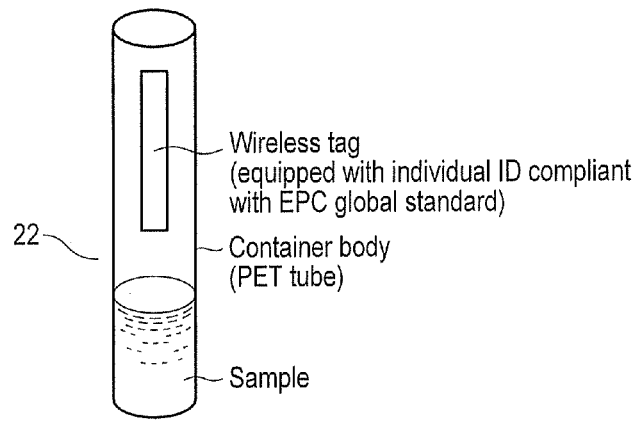
FIG. 29C is a perspective view showing an example of a container stored in the rack.

FIG. 29A, FIG. 29B, and FIG. 29C shows an example of how to detect the position of each of the containers 22 stored in the rack 21. A wireless tag 21A indicating a rack specification ID is affixed to the rack 21. This example is described using a rack that has five columns and ten rows. 50 first to fiftieth containers 22 with wireless tags are stored in the rack 21. Numbers 1 to 5 are given in the row direction and signs A to J are given in the column direction to indicate the positions of the containers 22 in the rack 21 by matrix coordinates. In this case, the wireless tag 21A which is the rack specification ID is affixed to the position corresponding to the origin (the row 1 and the column A).

Figure 30A:
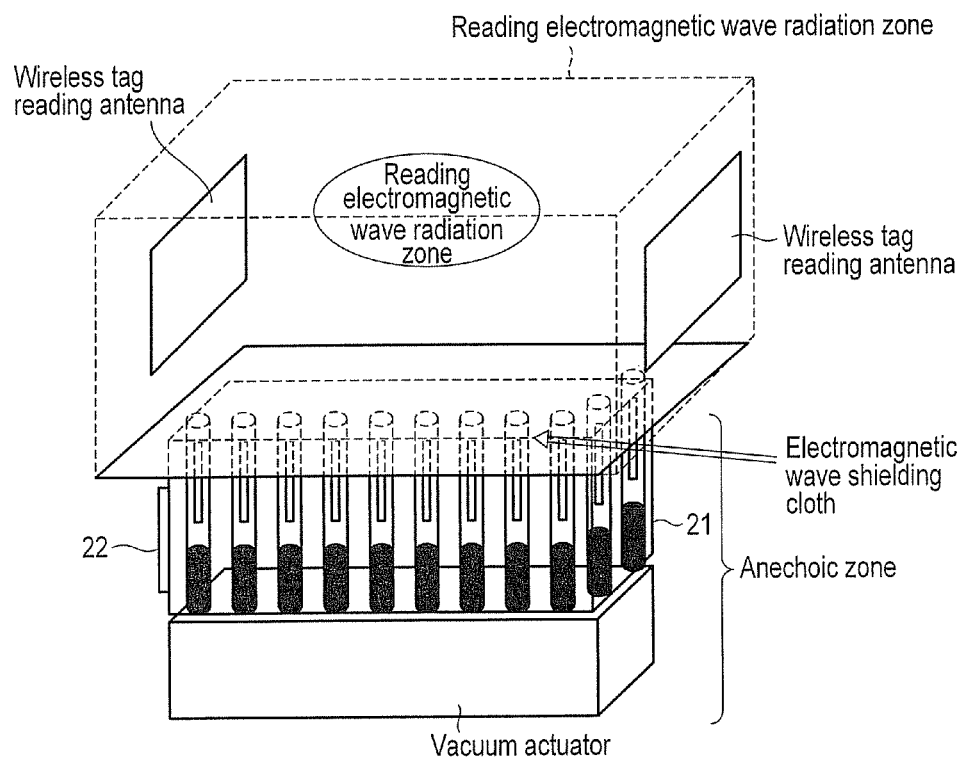
FIG. 30A is a diagram showing the overview of a container position detecting device.
Figure 30B:
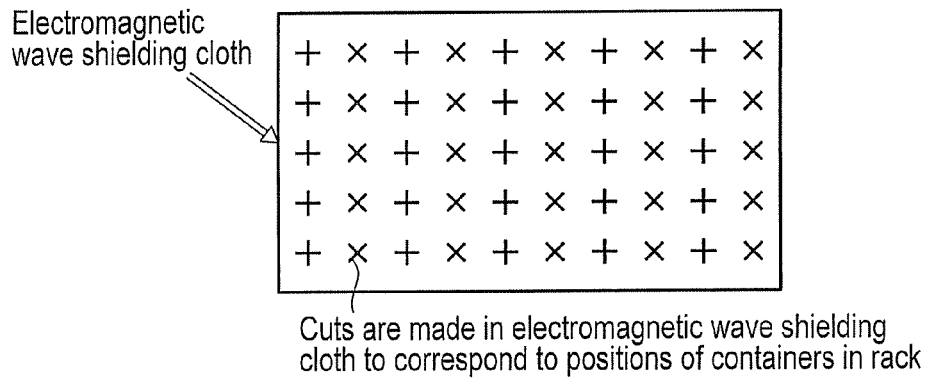
FIG. 30B is a diagram showing the overview of the container position detecting device.

FIG. 30A and FIG. 30B show the overview of a container position detecting device. An actuator is disposed under the rack 21, and the containers 22 in the rack 21 are pushed up one by one. Since the rack 21 is generally placed in an anechoic zone, the wireless tag reading antenna cannot read information in the wireless tag of the containers in the rack. A reading electromagnetic wave radiation zone is provided above the rack 21. The anechoic zone and the reading electromagnetic wave radiation zone are insulated, for example, by an electromagnetic wave shielding cloth or metal shutter with cuts.

More specifically, a vacuum actuator is disposed under the rack 21 along the arrangement pattern of the containers 22. The electromagnetic wave shielding cloth having cuts that allow the containers 22 to path there through are laid over the rack 21. The wireless tag reading antennas are disposed on both sides of the rack in the space above the rack 21. In the example shown, the space under the electromagnetic wave shielding cloth is in an anechoic chamber, and the space above the electromagnetic wave shielding cloth is the zone for the wireless tag reading radio wave radiation. Thus, the space can be electromagnetically separated.

Figure 31A:
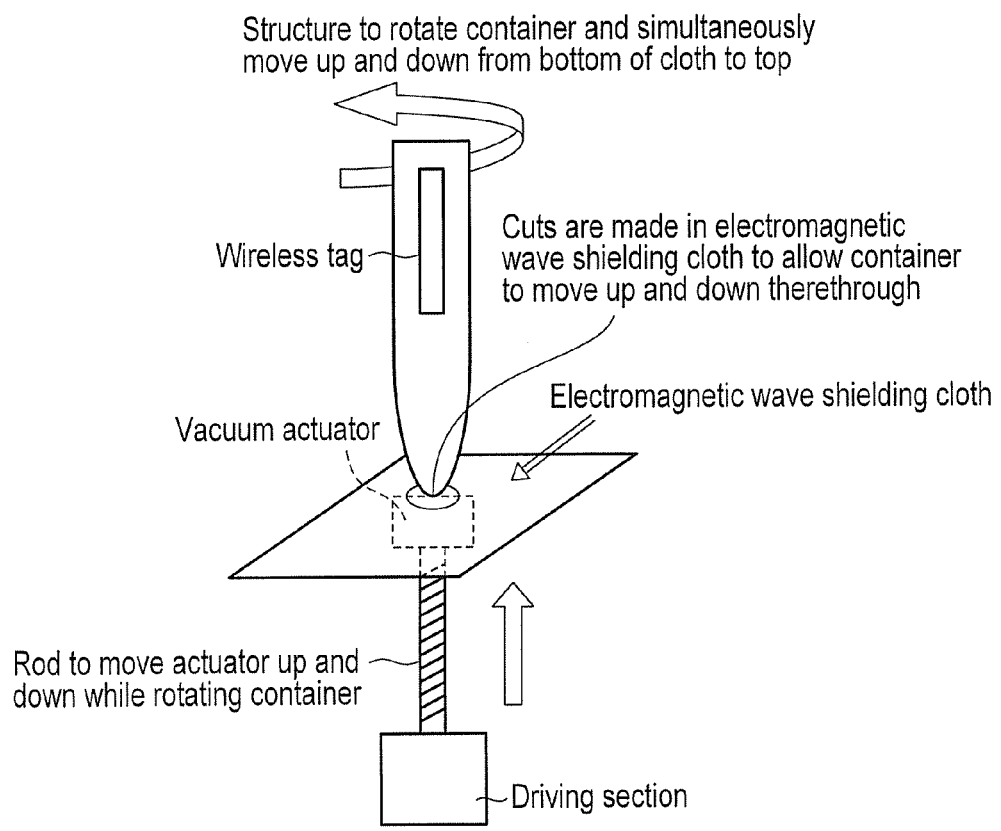
FIG. 31A is a diagram showing a container position specifying operation.

FIG. 31A and FIG. 31B show the operation for specifying the position of the container 22. This device is separated into an "anechoic region" and a "radio wave radiation region". The space between these regions is partitioned by an electromagnetic wave shielding cloth with cuts. The containers are inserted into a reading zone one by one in a rotating state via an actuator, and the IDs of the containers are read.

More specifically, the containers 22 in the rack 21 are pushed out from the bottom one by one by a vacuum actuator under the rack 21, and the container is pushed up in a rotating state into the radio wave radiation region through the cut in the radio wave shielding cloth. The container is pushed up in a rotating state to enhance the reaction of the tag in the electromagnetic waves.

The contents of the wireless tag of the container 22 are read, and data is stored in a management PC together with the position information, and then the actuator returns the container 22 to the rack 21. The end of the actuator is structured to stick to the bottom of the container 22. Thus, the containers 22 are repeatedly brought into the electromagnetic wave radiation zone in turn from the origin in the rack 21 to examine whether the wireless tags of all the containers 22 stored in the rack 21 function normally and acquire information on the positions of the containers 22.

FIG. 32 shows another configuration example of the position detecting device for the containers 22 in the rack. The rack is put in an anechoic chamber, and the containers 22 in the rack are pushed out one by one into the radio wave radiation zone as in FIG. 31A and FIG. 31B. However, in FIG. 32, there are actuators both under and above the rack 21. The actuator under the rack 21 is used to push out the container 22 into the electromagnetic wave radiation zone. The actuator above the rack 21 is used to return the container 22 to the anechoic zone. As a result, it is not necessary to provide a sticking mechanism at the end of the actuator.

That is, arranging container moving vacuum actuators under the bottoms of the containers 22 leads to increased costs and a complex structure. According to the configuration described above, only one actuator is mounted on the pillars freely movable in both X-axis and Y-axis directions. Moreover, the actuator is not only provided under the containers but the actuator is also provided above the containers. The container 22 is moved from both the upper and lower sides and thereby easily passes through the cut in the electromagnetic wave shielding cloth. The rack body is placed in the anechoic region. The container 22 pushed out by an actuator A (drawn out by an actuator B) is only brought into the electromagnetic wave radiation region, and the ID of its wireless tag is read. The container 22 may be fixed by using the pinching force of the actuators A and B, and a proper movable tray may be used together to stabilize the fixing.

Figure 33B:
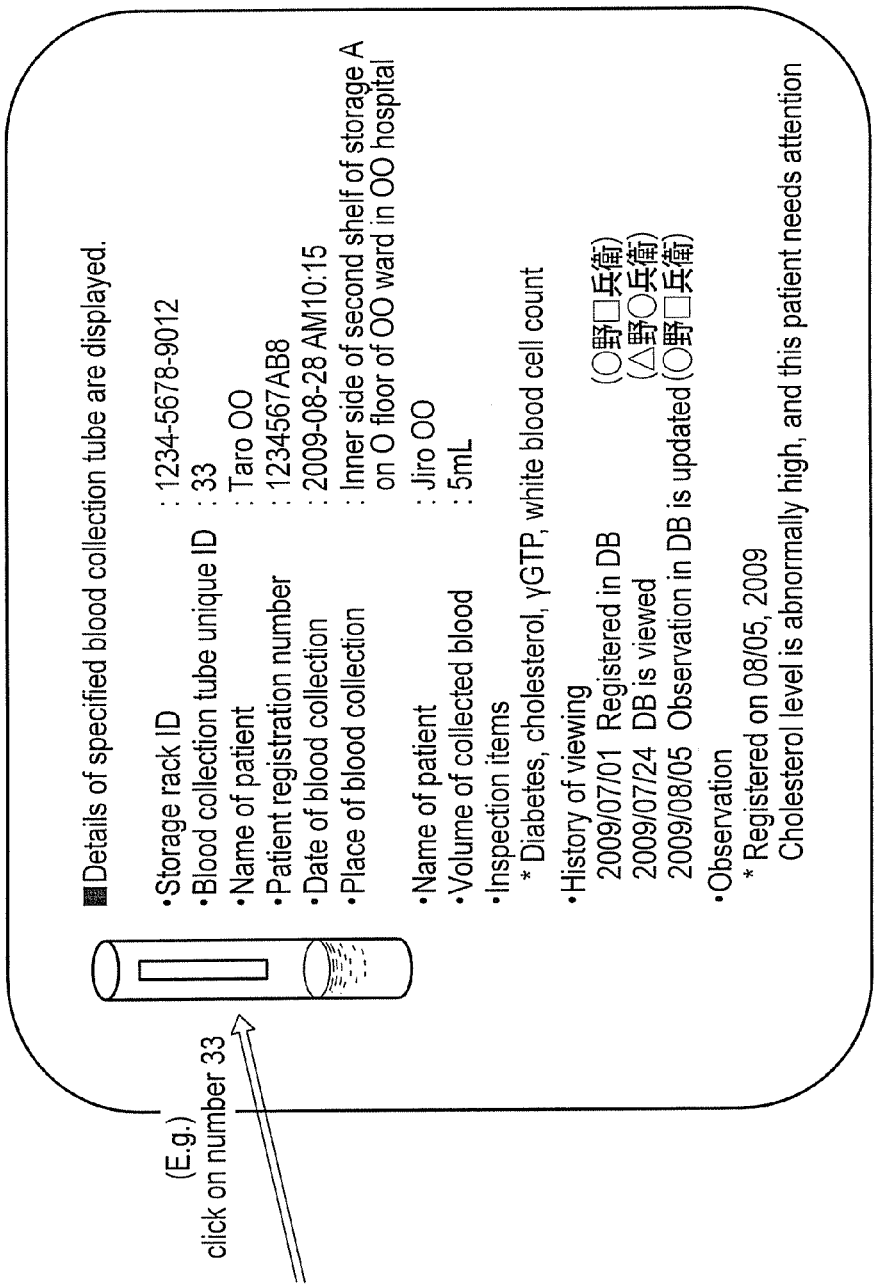
FIG. 33B is a diagram showing an example of how to display the rack-by-rack position detection information on the management PC.

FIG. 33A and FIG. 33B show an example of how to display position detection information for each rack 21 on the management PC. The place where the rack 21 is stored is indicated by a rack unique ID affixed to the rack 21. If a particular position in the rack 21 is designated, information in the wireless tag of the container (blood collection tube) stored at this position and management information attached to this wireless tag information are output onto a screen.

FIG. 34 shows how the wireless tag collective reading device according to the present invention communicates with a host server C6 via the Internet (IP network) C4. A test tube rack C1 is stored in a wireless tag collective reading device C2, and data in the wireless tag read by the wireless tag collective reading device C2 is sent to the server C6 set at an upper position of a network structure by an encrypted communication technique such as IPSec or SSL and by the functions of routers C3 and C5.

In the meantime, data is encrypted, and the communication pathway is secret, so that security is ensured. The server C6 set at the upper position has a database therein, and the information sent from each wireless tag collective reading device C2 can be stored in the database. A user having a proper ID and password can access this server C6, and search the stored wireless tag data from any position via the secret communication to view information in any tag from any position.

FIG. 35 shows an example to explain the traceability ensured by the wireless tag collective reading device according to the present invention. Although FIG. 35 shows an example of a blood test using a vacuum blood collection tube, the basic configuration remains the same for other products. A wireless tag is attached to the vacuum blood collection tube when manufactured. It should be understood that the wireless tag can also be affixed in the same manner as a seal as heretofore. At this point, the place where each blood collection tube is manufactured and the number of its wireless tag ID are registered on the host server.

The vacuum blood collection tubes are then shipped, and delivered to hospitals in various places. At the hospital, blood is collected from patients, and the vacuum blood collection tubes in which blood has been collected are sent to the host server via the automatic reading device according to the present invention. In this case, the hospital, time, and person corresponding to the collected blood are linked with the ID of the wireless tag.

The vacuum blood collection tubes are then stored in racks for the analysis of the blood, and sent to an analytical center rack by rack. In this case, the wireless tag collective reading device according to the present invention is used in the box shipment from the hospital to the analytical center and the box shipment from the analytical center to the hospital. Here, the wireless tags are collectively read rack by rack, and the history is stored in the host server in regard to, for example, the IDs of the wireless tags, the time when the wireless tags are delivered to the analytical center from the hospital, and the time when the wireless tags are returned to the hospital from the analytical center. It should be understood that the analysis is conducted in the analytical center and the analytical results are stored in the server so that information such as the ID and the kind of problem, if any, of the collected blood is managed and stored for each wireless tag ID.

Finally, the used vacuum blood collection tubes are sent to a medical waste treating company. At the medical waste treating company, the IDs of the wireless tags to be disposed of are sent to the host server by the wireless tag collective reading device according to the present invention immediately before disposal, and information on the properly completed disposal is stored in the database.

FIG. 36, FIG. 37, and FIG. 38 show an example of the process of a blood test in a general clinic to explain the embodiment according to the present invention.

In FIG. 36, (1) information initially registered on the database includes an EPC code, a blood collection tube manufacturer code, a blood collection tube expiration date, a blood test type code, a code of a used medical institution, an initial registration date, a registration place, and a registrant. (2) Information registered at the place where blood is collected includes EPC code reference for each blood collection tube (a judgment regarding the permission of the use of the blood collection tube, and a check against a medical record), personal information (e.g., name and age) for each person corresponding to the collected blood, an inspection item code (more than one items specified) for each blood collection tube, the date of the blood collection, the code of the medical institution where the blood is collected, a registration card number (when tied to an ordered medical record), the nurse who collected the blood, and a nurse code.

In FIG. 37, (3) information dealt with in the box shipment transaction includes an EPC code of each blood collection tube, an RF-ID code (rack number) attached to the rack, the shipment date, a code for the medical institution which has shipped the rack, a code for a sample test company to which the rack is shipped, the place of box shipment, and operators. (4) Information dealt with in the box shipment transaction at the sample test company includes an EPC code of each blood collection tube, an RF-ID code (rack number) attached to the rack, the arrival date, a code for the acceptor medical institution, the total number of arrived racks, the place of box shipment, and operators.

In FIG. 38, (5) transaction before a sample test includes reading of the EPC codes of the individual blood collection tubes, the confirmation and sorting of the inspection items, the registration of the inspection date, and the registration of the code of the used testing institution. (6) Transaction in the sample test includes reading of the EPC codes of the individual blood collection tubes, the implementation of the inspections in the inspection items, the registration of the inspection date, and the registration of the results in the database. (7) Transaction in the disposal of the sample includes reading of the EPC codes of the individual blood collection tubes, the registration of the disposal data, the registration of a disposal place code, and the registration of the disposal completion results in the database. (8) Transaction in the confirmation of the sample test results includes the search of the database by the name of a patient, the display and output of the test results, the confirmation of a test termination code, and the confirmation of a disposal termination code.

In FIG. 36, FIG. 37, and FIG. 38, a labeler is used to wind the wireless tag around the vacuum blood collection tube serving as a container. In this condition, the wireless tag IDs of the vacuum blood collection tubes are read by using the wireless tag collective reading device according to the present invention, and are stored in the database of the host PC. The vacuum blood collection tubes with the wireless tags are stored in the medical institution in this condition. A necessary number of vacuum blood collection tubes are taken out when necessary, for example, when blood is collected. In the number of vacuum blood collection tubes necessary for blood collection, the personal information for each patient is registered by an information registration PC at the blood collection site immediately before the blood collection. The vacuum blood collection tubes in which blood has been collected are then put together in a rack and wait for the shipment to the sample test company.

At the shipment to the sample test company, the collective reading device according to the present invention is used for the box shipment transaction, and information including the patient, the blood collection tube, and the time when the blood collection tube is sent to the sample test company are stored in the host management server.

At the sample test company, the collective reading device according to the present invention is used in the box shipment procedure at the time of acceptance to record the medical institution from which the blood collection tubes are arrived, and the number of the blood collection tubes. In the actual sample test, an automatic conveyer is used to move the blood collection tubes one by one, and the contents of the wireless tag affixed to each of the blood collection tubes are read by a vacuum blood collection tube individual reading device. In accordance with the contents of the wireless tag, a prescribed inspection process is carried out by an automatic dispensing tester, and the results are stored in the database of the management PC.

The blood collection tubes after the end of the inspection are disposed of. In this case, information regarding which blood collection tube has been disposed of is acquired by using the collective reading device according to the present invention, and registered in the host management PC as disposed tube information. The clinic can access the host management PC to view, on a terminal, the test results for the patient.

Figure 39A:
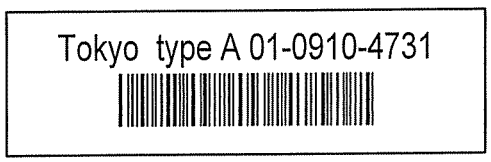
FIG. 39A is a top view showing the structure of a bar code printed on and inlaid in a label surface of a wireless tag.
Figure 39B:
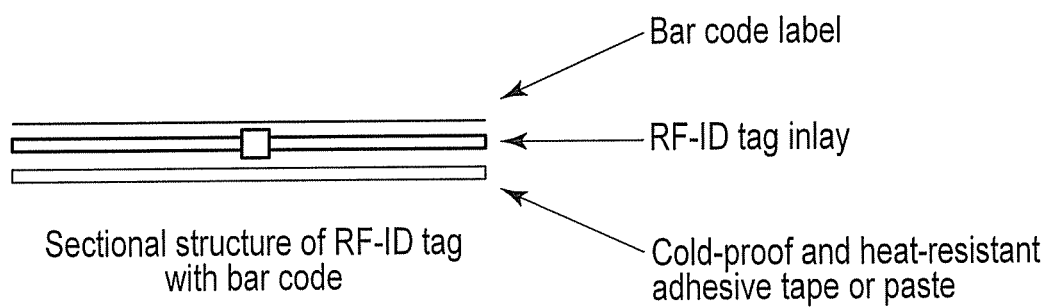
FIG. 39B is a sectional view showing the structure of the bar code printed on and inlaid in the label surface of the wireless tag.

FIG. 39A, FIG. 39B, FIG. 39C, FIG. 39D, and FIG. 39E each show the structure of a bar code printed on and inlaid in a label surface of a wireless tag. FIG. 39A shows a top view. FIG. 39B shows a sectional view. FIG. 39C shows an example of a bar code label. FIG. 39D shows an example of an RF-ID tag inlay. FIG. 39E shows a layer comprising a cold-proof and heat-resistant adhesive tape or paste.

That is, according to the above structure, the bar code is used in addition to the management that only uses the wireless tags. Thus, traceability can be ensured even when the wireless tag is broken in an article delivery process or even in a place where no environment is available to read the wireless tag.

FIG. 40 shows an example of how to deal with a broken wireless tag. In the case shown here, there is a vacuum blood collection tube with a broken wireless tag affixed thereto that is found when individual information is registered before blood collection. There are two ways to deal with the situation. One way is to affix a new wireless tag. The other way is to manage by using a bar code reading device when a bar code is printed on the label surface of the wireless tag.

An example of traceability using the vacuum blood collection tube has been shown above. If a vacuum blood collection tube that cannot be read is found during the above-described process, its wireless tag is regarded as broken, and a new wireless tag is affixed to give a new ID. At the same time, the new ID is linked with the prior data on the server side, such that 100% traceability can be ensured.

It should be noted that this invention is not completely limited to the embodiment described above, and modifications of components can be made at the stage of carrying out the invention without departing from the spirit thereof. Further, various inventions can be made by properly combining the components disclosed in the embodiment described above. For example, some of all the components shown in the embodiment may be eliminated. Moreover, components in different embodiments may be suitably combined together.

The present invention is suitably applicable particularly to a device for reading, by radio waves, all wireless tags attached to closely arranged articles such as containers including test tubes or vacuum blood collection tubes.

What is claimed is:

1. A wireless tag collective reading device for collectively reading tag information from articles equipped with wireless tags each emitting the tag information in response to an electromagnetic wave, the device comprising:

a rack which comprises storage areas to store the articles;

an antenna unit which applies the electromagnetic waves to the articles stored in the rack, and receives the tag information emitted from the wireless tags;

an electromagnetic wave controller which controls directivity, intensity, and phase of the electromagnetic waves emitted from the antenna unit;

a position controller which controls relative positions of the antenna unit and the rack;

a reader which reads the tag information from a signal received by the antenna unit;

an article detector which detects whether the articles are stored in the storage areas in the rack, respectively;

a counter which counts a total number of the articles stored in the storage areas in the rack from a detection result of the article detector; and a checking unit which checks number of pieces of the tag information read by the reader against the number of the stored articles counted by the counter.

2. The device according to claim 1, wherein the checking unit determines from a result of the checking, whether the tag information of the wireless tags applied to all of the articles stored in the rack has been correctly read, or whether any reading error has occurred, or how many wireless tags have been unsuccessfully read if reading errors have occurred.

3. The device according to claim 1, wherein if the number of pieces of the read tag information does not correspond to the number of the stored articles, the checking unit urges the electromagnetic wave controller to change the directivity, phase, and radiation intensity of the electromagnetic waves, and specifies an article that has not been normally read and the place of storage of the article, from a reading result of the reader and a detection result of the article detector.

4. The device according to claim 1, further comprising an article conveying mechanism which discharges the articles one by one and arranges the discharged articles in an application area of the electromagnetic wave in a state in which the rack is arranged in an electromagnetic wave anechoic chamber shielding the electromagnetic wave emitted from the antenna unit, and returns the articles to the rack after reading the tag information of the articles has been completed, wherein if the number of pieces of the read tag information does not correspond to the number of the stored articles, the checking unit discharges the articles one by one from the rack arranged in the electromagnetic wave anechoic chamber and automatically arranges the discharged articles in the application area of the electromagnetic wave by the article conveying mechanism, automatically reads the tag information of the articles, and specifies an article which has not been normally read and a position of the article in the rack.

5. The device according to claim 1, further comprising:

an information processing unit which collects position information of the articles stored in the rack from a detection result of the article detector, and associates the tag information which has been successfully read and unreadable information which has not been read with the position information of the articles; and a management server which is connected to the information processing unit via a network and which comprises a database registering and managing the information on each of the articles collected by the information processing unit, wherein the management server ties arbitrary management information to the information of each of the articles registered in the database and registers the information.

6. The device according to claim 5, wherein when identification information labels indicating the tag information are applied to the articles together with the wireless tags, the management server rewrites unreadable information of the database to tag information which is read from an identification information label applied to an article associated with the unreadable information, of the articles registered in the database.

7. A network article management system comprising:

the wireless tag collective reading device according to any one of claims 1 to 6; and a host management server connected to the wireless tag collective reading device via a network to store and manage the information collected by the reading device, wherein the host management server ensures traceability of each of the articles from a manufacturing stage to a usage stage and a disposal stage on the basis of the stored information and, if impossibility to receive the tag information is detected, registers tag information from a wireless tag newly applied to the article.

* * * * *